US 9,278,180 B2

(12) United States Patent
Wong

(10) Patent No.: US 9,278,180 B2
(45) Date of Patent: Mar. 8, 2016

(54) NEEDLE SAFETY DEVICE

(75) Inventor: Andrew Wong, Philadelphia, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 855 days.

(21) Appl. No.: 12/275,570

(22) Filed: Nov. 21, 2008

(65) Prior Publication Data

US 2009/0157013 A1 Jun. 18, 2009

Related U.S. Application Data

(60) Provisional application No. 60/989,466, filed on Nov. 21, 2007.

(51) Int. Cl.
*A61M 5/32* (2006.01)
*A61B 17/34* (2006.01)
*A61B 19/00* (2006.01)

(52) U.S. Cl.
CPC .......... *A61M 5/3273* (2013.01); *A61B 17/3401* (2013.01); *A61B 2019/4805* (2013.01); *A61M 2005/3201* (2013.01);
(Continued)

(58) Field of Classification Search
CPC ..... A61M 5/32; A61M 5/321; A61M 5/1626; A61M 5/3243; A61M 5/3273; A61M 2005/14256; A61M 2005/1426; A61M 25/0612; A61M 2039/042; A61M 25/0618; A61M 2005/3247; A61M 2005/3249; A61M 2005/325
USPC ......... 604/110, 158, 164.09, 164.1, 192, 198, 604/263
See application file for complete search history.

(56) References Cited

U.S. PATENT DOCUMENTS

| 3,175,554 A | 3/1965 | Stewart |
| 3,515,137 A | 6/1970 | Santomieri |
| 4,405,307 A | 9/1983 | Taylor |

(Continued)

FOREIGN PATENT DOCUMENTS

| DE | 202007006190 U1 | 8/2007 |
| EP | 0750915 A | 1/1997 |

(Continued)

OTHER PUBLICATIONS

U.S. Appl. No. 12/275,604, filed Nov. 21, 2008, Meehan et al.

(Continued)

*Primary Examiner* — Bhisma Mehta
*Assistant Examiner* — Larry R Wilson
(74) *Attorney, Agent, or Firm* — The Webb Law Firm

(57) ABSTRACT

A needle guard having a housing defining an interior cavity, and a transitional member disposed within the interior cavity is disclosed. The transitional member includes a pivoting arm having a first end and a second end, the first end adjacent an interior portion of the housing. The transitional member also includes a needle tip sensing element, and a transverse barrier, such that the needle tip sensing element and the transverse barrier are oriented on opposing sides of the pivoting arm adjacent the second end. The needle guard may be adapted for transition from a restrained position when the needle tip is exterior to the interior cavity, to an activated position when the needle tip is within the interior cavity. The transitional member may also have a needle tip sensing element for contacting a needle in the restrained position, and a binding edge for engaging the needle in the activated position.

34 Claims, 14 Drawing Sheets

(52) U.S. Cl.
CPC . *A61M 2005/325* (2013.01); *A61M 2005/3247* (2013.01); *A61M 2005/3249* (2013.01)

(56) References Cited

U.S. PATENT DOCUMENTS

| | | | |
|---|---|---|---|
| 4,565,545 A | 1/1986 | Suzuki | |
| 4,588,398 A | 5/1986 | Daugherty et al. | |
| 4,609,370 A | 9/1986 | Morrison | |
| 4,721,506 A | 1/1988 | Teves | |
| 4,755,170 A | 7/1988 | Golden | |
| 4,778,453 A | 10/1988 | Lopez | |
| 4,790,828 A | 12/1988 | Dombrowski et al. | |
| 4,795,432 A | 1/1989 | Karczmer | |
| 4,799,495 A | 1/1989 | Hawkins et al. | |
| 4,804,371 A | 2/1989 | Vaillancourt | |
| 4,846,811 A | 7/1989 | Vanderhoof | |
| 4,863,439 A | 9/1989 | Sanderson | |
| 4,869,259 A | 9/1989 | Elkins | |
| 4,929,241 A * | 5/1990 | Kulli | 604/263 |
| 4,931,048 A | 6/1990 | Lopez | |
| 4,944,725 A | 7/1990 | McDonald | |
| 4,952,207 A | 8/1990 | Lemieux | |
| 4,955,866 A | 9/1990 | Corey | |
| 4,964,854 A | 10/1990 | Luther | |
| 4,966,583 A | 10/1990 | Debbas | |
| 5,009,642 A | 4/1991 | Sahi | |
| 5,013,305 A | 5/1991 | Opie et al. | |
| 5,015,242 A | 5/1991 | Heifetz | |
| 5,049,136 A | 9/1991 | Johnson | |
| 5,053,017 A | 10/1991 | Chamuel | |
| 5,059,180 A | 10/1991 | McLees | |
| 5,106,376 A | 4/1992 | Mononen et al. | |
| 5,120,317 A | 6/1992 | Luther | |
| 5,120,321 A | 6/1992 | Oksman et al. | |
| 5,135,504 A | 8/1992 | McLees | |
| 5,141,497 A | 8/1992 | Erskine | |
| 5,147,327 A | 9/1992 | Johnson | |
| 5,149,324 A | 9/1992 | Clawson | |
| 5,171,229 A * | 12/1992 | McNeil et al. | 604/192 |
| 5,176,655 A | 1/1993 | McCormick et al. | |
| 5,183,468 A | 2/1993 | McLees | |
| 5,186,712 A | 2/1993 | Kelso et al. | |
| 5,217,438 A | 6/1993 | Davis et al. | |
| RE34,416 E | 10/1993 | Lemieux | |
| 5,263,936 A | 11/1993 | Yurino | |
| 5,279,570 A | 1/1994 | Dombrowski et al. | |
| 5,295,963 A | 3/1994 | Deeks | |
| 5,295,974 A | 3/1994 | O'Laughlin | |
| 5,300,045 A | 4/1994 | Plassche, Jr. | |
| 5,304,151 A | 4/1994 | Kuracina | |
| 5,314,503 A | 5/1994 | Bobrove et al. | |
| 5,322,517 A | 6/1994 | Sircom et al. | |
| 5,328,482 A | 7/1994 | Sircom et al. | |
| 5,330,432 A | 7/1994 | Yoon | |
| 5,334,158 A | 8/1994 | McLees | |
| 5,334,161 A | 8/1994 | Gurmarnik | |
| 5,336,176 A | 8/1994 | Yoon | |
| 5,336,191 A | 8/1994 | Davis et al. | |
| 5,344,408 A | 9/1994 | Partika | |
| 5,385,561 A | 1/1995 | Cerny | |
| 5,401,247 A | 3/1995 | Yoon | |
| 5,419,766 A | 5/1995 | Chang et al. | |
| 5,425,720 A | 6/1995 | Rogalsky et al. | |
| 5,425,721 A | 6/1995 | Malenchek | |
| 5,433,711 A | 7/1995 | Balaban et al. | |
| 5,458,658 A | 10/1995 | Sircom | |
| 5,466,225 A | 11/1995 | Davis et al. | |
| 5,484,423 A | 1/1996 | Waskönig et al. | |
| 5,501,672 A | 3/1996 | Firth et al. | |
| 5,514,114 A | 5/1996 | Soto-Tolosa et al. | |
| 5,533,974 A | 7/1996 | Gaba | |
| 5,533,975 A | 7/1996 | Lu | |
| 5,549,570 A | 8/1996 | Rogalsky | |
| 5,558,651 A | 9/1996 | Crawford et al. | |
| 5,562,633 A | 10/1996 | Wozencroft | |
| 5,569,217 A | 10/1996 | Luther | |
| 5,571,091 A | 11/1996 | Davis et al. | |
| 5,584,809 A | 12/1996 | Gaba | |
| 5,584,818 A | 12/1996 | Morrison | |
| 5,599,310 A | 2/1997 | Bogert | |
| 5,601,532 A | 2/1997 | Gaba | |
| 5,611,781 A | 3/1997 | Sircom et al. | |
| 5,630,802 A | 5/1997 | Moellmann et al. | |
| 5,662,610 A | 9/1997 | Sircom | |
| 5,683,365 A | 11/1997 | Brown et al. | |
| 5,683,368 A | 11/1997 | Schmidt | |
| 5,683,370 A | 11/1997 | Luther et al. | |
| 5,697,907 A | 12/1997 | Gaba | |
| 5,718,688 A | 2/1998 | Wozencroft | |
| 5,725,504 A | 3/1998 | Collins | |
| 5,741,233 A | 4/1998 | Riddle et al. | |
| 5,743,882 A | 4/1998 | Luther | |
| 5,743,891 A | 4/1998 | Tolkoff et al. | |
| 5,746,718 A | 5/1998 | Steyn | |
| 5,755,699 A | 5/1998 | Blecher et al. | |
| 5,817,060 A | 10/1998 | Overton et al. | |
| 5,833,670 A | 11/1998 | Dillon et al. | |
| 5,846,226 A | 12/1998 | Urmey | |
| 5,853,393 A | 12/1998 | Bogert | |
| 5,879,337 A | 3/1999 | Kuracina et al. | |
| 5,882,337 A | 3/1999 | Bogert et al. | |
| 5,891,093 A | 4/1999 | Dysarz | |
| 5,910,132 A | 6/1999 | Schultz | |
| 5,913,848 A | 6/1999 | Luther et al. | |
| 5,916,208 A | 6/1999 | Luther et al. | |
| 5,951,529 A | 9/1999 | Utterberg | |
| 6,001,080 A | 12/1999 | Kuracina et al. | |
| 6,004,294 A | 12/1999 | Brimhall et al. | |
| 6,080,135 A | 6/2000 | Van Stokkum | |
| RE36,885 E | 9/2000 | Blecher et al. | |
| 6,117,108 A | 9/2000 | Woehr et al. | |
| 6,120,480 A | 9/2000 | Zhang et al. | |
| 6,132,402 A | 10/2000 | Tessmann et al. | |
| 6,165,157 A | 12/2000 | Dillon et al. | |
| 6,203,527 B1 | 3/2001 | Zadini et al. | |
| 6,210,372 B1 | 4/2001 | Tessmann et al. | |
| 6,210,373 B1 * | 4/2001 | Allmon | 604/192 |
| 6,221,047 B1 | 4/2001 | Greene et al. | |
| 6,235,001 B1 | 5/2001 | O'Holloran et al. | |
| 6,235,006 B1 | 5/2001 | Dillon et al. | |
| 6,280,419 B1 | 8/2001 | Vojtasek | |
| 6,287,278 B1 | 9/2001 | Woehr et al. | |
| 6,322,537 B1 | 11/2001 | Chang | |
| 6,379,332 B1 | 4/2002 | Van Landuyt | |
| 6,379,333 B1 | 4/2002 | Brimhall et al. | |
| 6,406,459 B1 | 6/2002 | Allmon | |
| 6,443,927 B1 | 9/2002 | Cook | |
| 6,443,929 B1 | 9/2002 | Kuracina et al. | |
| 6,475,189 B1 | 11/2002 | Lilley, Jr. | |
| 6,485,468 B2 | 11/2002 | Vojtasek | |
| 6,500,153 B1 | 12/2002 | Sheppard et al. | |
| 6,500,157 B2 | 12/2002 | Luther | |
| 6,520,938 B1 | 2/2003 | Funderburk et al. | |
| 6,558,353 B2 | 5/2003 | Zohmann | |
| 6,585,704 B2 | 7/2003 | Luther et al. | |
| 6,595,954 B1 | 7/2003 | Luther et al. | |
| 6,595,955 B2 | 7/2003 | Ferguson et al. | |
| 6,616,630 B1 | 9/2003 | Woehr et al. | |
| 6,623,458 B2 | 9/2003 | Woehr et al. | |
| 6,629,959 B2 | 10/2003 | Kuracina et al. | |
| 6,641,564 B1 | 11/2003 | Kraus | |
| 6,652,486 B2 | 11/2003 | Bialecki et al. | |
| 6,652,490 B2 | 11/2003 | Howell | |
| 6,663,592 B2 | 12/2003 | Rhad et al. | |
| 6,689,102 B2 | 2/2004 | Greene | |
| 6,692,471 B2 | 2/2004 | Boudreaux | |
| 6,695,814 B2 | 2/2004 | Greene et al. | |
| 6,709,419 B2 | 3/2004 | Woehr | |
| 6,709,428 B2 | 3/2004 | Sagstetter | |
| 6,749,588 B1 | 6/2004 | Howell et al. | |
| 6,761,706 B2 | 7/2004 | Vaillancourt | |
| 6,786,875 B2 | 9/2004 | Barker et al. | |
| 6,796,962 B2 | 9/2004 | Ferguson et al. | |
| 6,811,545 B2 | 11/2004 | Vaillancourt | |

(56) References Cited

U.S. PATENT DOCUMENTS

| | | | |
|---|---|---|---|
| 6,837,878 B2 | 1/2005 | Smutney et al. |
| 6,860,871 B2 | 3/2005 | Kuracina et al. |
| 6,863,659 B2 | 3/2005 | Sharpe |
| 6,902,546 B2 | 6/2005 | Ferguson |
| 6,916,311 B2 | 7/2005 | Vojtasek |
| 6,923,793 B2 | 8/2005 | Ishida et al. |
| 6,972,002 B2 | 12/2005 | Thorne |
| 6,981,965 B2 | 1/2006 | Luther et al. |
| 6,984,213 B2 | 1/2006 | Horner et al. |
| RE38,996 E | 2/2006 | Crawford et al. |
| 7,004,927 B2 | 2/2006 | Ferguson et al. |
| 7,008,402 B2 | 3/2006 | Ferguson et al. |
| 7,018,344 B2 | 3/2006 | Bressler et al. |
| 7,024,749 B2 | 4/2006 | Sagstetter |
| 7,083,600 B2 | 8/2006 | Meloul |
| 7,112,191 B2 | 9/2006 | Daga |
| 7,125,397 B2 | 10/2006 | Woehr et al. |
| 7,150,725 B2 | 12/2006 | Wilkinson |
| 7,153,276 B2 | 12/2006 | Barker et al. |
| 7,160,269 B2 | 1/2007 | Woehr |
| 7,179,244 B2 | 2/2007 | Smith et al. |
| 7,186,239 B2 | 3/2007 | Woehr |
| 7,207,975 B2 | 4/2007 | Miller |
| 7,214,208 B2 | 5/2007 | Vaillancourt |
| 7,214,211 B2 | 5/2007 | Woehr et al. |
| 7,226,434 B2 | 6/2007 | Carlyon et al. |
| 7,238,169 B2 | 7/2007 | Takagi et al. |
| 7,247,148 B2 | 7/2007 | Murashita |
| 7,255,685 B2 | 8/2007 | Pressly, Sr. et al. |
| 7,264,613 B2 | 9/2007 | Woehr et al. |
| 7,753,877 B2 * | 7/2010 | Bialecki et al. | 604/110 |
| 7,935,080 B2 | 5/2011 | Howell et al. |
| 2001/0014786 A1 | 8/2001 | Greene et al. |
| 2001/0018573 A1 | 8/2001 | Woehr |
| 2001/0027298 A1 | 10/2001 | Vojtasek |
| 2001/0029356 A1 | 10/2001 | Vojtasek |
| 2001/0053895 A1 | 12/2001 | Vaillancourt |
| 2002/0004650 A1 | 1/2002 | Kuracina et al. |
| 2002/0045843 A1 | 4/2002 | Barker et al. |
| 2002/0099335 A1 | 7/2002 | Zohmann |
| 2002/0103463 A1 | 8/2002 | Luther et al. |
| 2002/0151850 A1 | 10/2002 | Ferguson et al. |
| 2002/0165497 A1 | 11/2002 | Greene |
| 2002/0169418 A1 | 11/2002 | Menzi et al. |
| 2002/0177818 A1 | 11/2002 | Vaillancourt |
| 2002/0193745 A1 | 12/2002 | Ferguson |
| 2003/0004471 A1 | 1/2003 | Hung et al. |
| 2003/0018301 A1 | 1/2003 | Sheppard et al. |
| 2003/0040710 A1 | 2/2003 | Polidoro |
| 2003/0060771 A1 | 3/2003 | Bialecki et al. |
| 2003/0060774 A1 | 3/2003 | Woehr et al. |
| 2003/0100868 A1 | 5/2003 | Ferguson et al. |
| 2003/0105431 A1 | 6/2003 | Howell |
| 2003/0109833 A1 | 6/2003 | Sharpe |
| 2003/0114797 A1 | 6/2003 | Vaillancourt et al. |
| 2003/0120222 A1 | 6/2003 | Vaillancourt |
| 2003/0144627 A1 | 7/2003 | Woehr et al. |
| 2003/0171718 A1 | 9/2003 | DeLegge et al. |
| 2003/0195471 A1 | 10/2003 | Woehr et al. |
| 2003/0195475 A1 | 10/2003 | Ferguson et al. |
| 2003/0195479 A1 | 10/2003 | Kuracina et al. |
| 2003/0216687 A1 | 11/2003 | Hwang |
| 2003/0220617 A1 | 11/2003 | Dickerson |
| 2004/0010227 A1 | 1/2004 | Riesenberger et al. |
| 2004/0030289 A1 | 2/2004 | Vitullo et al. |
| 2004/0049155 A1 | 3/2004 | Schramm |
| 2004/0049163 A1 * | 3/2004 | Murashita | 604/263 |
| 2004/0078002 A1 | 4/2004 | Rhad et al. |
| 2004/0078003 A1 | 4/2004 | Smith et al. |
| 2004/0092879 A1 | 5/2004 | Kraus et al. |
| 2004/0092885 A1 | 5/2004 | Duchon et al. |
| 2004/0092889 A1 * | 5/2004 | Ferguson et al. | 604/263 |
| 2004/0102740 A1 | 5/2004 | Meloul |
| 2004/0116856 A1 | 6/2004 | Woehr et al. |
| 2004/0116864 A1 | 6/2004 | Boudreaux |
| 2004/0122380 A1 | 6/2004 | Utterberg |
| 2004/0133167 A1 | 7/2004 | Ferguson et al. |
| 2004/0138628 A1 | 7/2004 | Woehr |
| 2004/0162522 A1 | 8/2004 | Woehr |
| 2004/0162525 A1 | 8/2004 | Vaillancourt et al. |
| 2004/0162526 A1 | 8/2004 | Vaillancourt et al. |
| 2004/0171989 A1 | 9/2004 | Horner et al. |
| 2004/0186434 A1 | 9/2004 | Harding et al. |
| 2004/0204681 A1 | 10/2004 | Thoresen et al. |
| 2004/0225260 A1 | 11/2004 | Villa et al. |
| 2004/0236289 A1 | 11/2004 | Ferguson et al. |
| 2004/0243061 A1 | 12/2004 | McGurk |
| 2005/0004521 A1 | 1/2005 | Zohmann |
| 2005/0004532 A1 | 1/2005 | Woehr et al. |
| 2005/0027256 A1 | 2/2005 | Barker et al. |
| 2005/0027263 A1 | 2/2005 | Woehr et al. |
| 2005/0043691 A1 | 2/2005 | Ferguson |
| 2005/0049559 A1 | 3/2005 | Mathias |
| 2005/0059937 A1 | 3/2005 | Ferguson |
| 2005/0070855 A1 | 3/2005 | Ferguson et al. |
| 2005/0075609 A1 | 4/2005 | Latona |
| 2005/0096592 A1 | 5/2005 | Carlyon et al. |
| 2005/0113755 A1 | 5/2005 | Greene et al. |
| 2005/0113758 A1 | 5/2005 | Smutney et al. |
| 2005/0182362 A1 | 8/2005 | Sircom et al. |
| 2005/0182363 A1 | 8/2005 | Kulli |
| 2005/0182369 A1 | 8/2005 | Miller |
| 2005/0192535 A1 | 9/2005 | Takagi et al. |
| 2005/0192536 A1 | 9/2005 | Takagi et al. |
| 2005/0273057 A1 | 12/2005 | Popov |
| 2005/0277879 A1 | 12/2005 | Daga |
| 2006/0041231 A1 | 2/2006 | Pressly, Sr. et al. |
| 2006/0058742 A1 | 3/2006 | Cha et al. |
| 2006/0074384 A1 | 4/2006 | Kohler |
| 2006/0079844 A1 | 4/2006 | Whisson et al. |
| 2006/0116638 A1 | 6/2006 | Woehr et al. |
| 2006/0129101 A1 | 6/2006 | McGuckin, Jr. |
| 2006/0155244 A1 | 7/2006 | Popov |
| 2006/0155245 A1 | 7/2006 | Woehr |
| 2006/0155246 A1 | 7/2006 | Higuchi et al. |
| 2006/0161116 A1 | 7/2006 | Willis et al. |
| 2006/0178635 A1 | 8/2006 | Callaway |
| 2006/0184116 A1 | 8/2006 | Takagi et al. |
| 2006/0184125 A1 | 8/2006 | Woehr |
| 2006/0189934 A1 | 8/2006 | Kuracina et al. |
| 2006/0264828 A1 | 11/2006 | Woehr et al. |
| 2006/0270980 A1 | 11/2006 | Menzi et al. |
| 2007/0038179 A1 | 2/2007 | Bialecki et al. |
| 2007/0038181 A1 | 2/2007 | Melamud et al. |
| 2007/0038182 A1 | 2/2007 | Bialecki et al. |
| 2007/0038183 A1 | 2/2007 | Bialecki et al. |
| 2007/0038184 A1 | 2/2007 | Bialecki et al. |
| 2007/0038185 A1 | 2/2007 | Albert et al. |
| 2007/0038186 A1 | 2/2007 | Sutton et al. |
| 2007/0038187 A1 | 2/2007 | Albert et al. |
| 2007/0038188 A1 | 2/2007 | Bialecki et al. |
| 2007/0049868 A1 | 3/2007 | Woehr et al. |
| 2007/0055203 A1 | 3/2007 | Miller |
| 2007/0060889 A1 | 3/2007 | Adams |
| 2007/0073221 A1 | 3/2007 | Bialecki et al. |
| 2007/0073222 A1 | 3/2007 | Lilley, Jr. et al. |
| 2007/0083159 A1 | 4/2007 | Woehr et al. |
| 2007/0083167 A1 | 4/2007 | Smith et al. |
| 2007/0100297 A1 | 5/2007 | Woehr et al. |
| 2007/0106231 A1 | 5/2007 | Snow et al. |
| 2007/0112305 A1 | 5/2007 | Brimhall |
| 2007/0129689 A1 | 6/2007 | Woehr et al. |
| 2007/0149928 A1 | 6/2007 | Kulli |
| 2007/0156093 A1 | 7/2007 | Woehr |
| 2007/0161950 A1 | 7/2007 | Carlyon et al. |
| 2007/0179446 A1 | 8/2007 | Carrez et al. |
| 2007/0179447 A1 | 8/2007 | Carrez et al. |
| 2007/0191771 A1 | 8/2007 | Moyer |
| 2007/0191775 A1 | 8/2007 | Diep et al. |
| 2007/0191776 A1 | 8/2007 | Bialecki et al. |
| 2007/0191777 A1 | 8/2007 | King |

(56) References Cited

U.S. PATENT DOCUMENTS

| | | |
|---|---|---|
| 2007/0191782 A1 | 8/2007 | Wilkinson |
| 2007/0232995 A1 | 10/2007 | Samsoondar |
| 2007/0250057 A1 | 10/2007 | Nobis et al. |

FOREIGN PATENT DOCUMENTS

| | | |
|---|---|---|
| EP | 1344544 A | 9/2003 |
| EP | 1752182 A | 2/2007 |
| JP | 7148255 A | 6/1995 |
| JP | 2005529717 A | 10/2005 |
| WO | 0110488 A | 2/2001 |
| WO | 02076526 A | 10/2002 |
| WO | 2005042073 A | 5/2005 |
| WO | 2005079891 A | 9/2005 |
| WO | 2005082439 A | 9/2005 |
| WO | 2008052791 A1 | 5/2008 |

OTHER PUBLICATIONS

U.S. Appl. No. 12/313,661, filed Nov. 21, 2008, Meehan et al.
U.S. Appl. No. 12/275,636, filed Nov. 21, 2008, Delano et al.

\* cited by examiner

NEEDLE SAFETY DEVICE

CROSS REFERENCE TO RELATED APPLICATION

This application claims priority to U.S. Provisional Patent Application No. 60/989,466, filed Nov. 21, 2007, entitled "Needle Safety Device", the entire disclosure of which is herein incorporated by reference.

BACKGROUND OF THE INVENTION

1. Field of the Invention

The subject invention relates generally to medical needles and, more particularly, to medical needles having a safety device for shielding the needle tip after withdrawal of the needle from a patient.

2. Description of Related Art

In order to adequately protect medical practitioners from inadvertent puncture and/or wounding from medical sharps, such as needles and syringes, safety shielding devices have been developed to limit the exposure from contaminated medical devices. In many procedures, the greatest avoidable risk of accidental needle puncture, also referred to as a "needlestick", occurs during handling of the used needle, such as when a medical practitioner inserts the used needle into a protective sheath for disposal. This action usually requires the practitioner to move the hand which holds the sheath toward the needle tip. Any inaccuracy in this movement increases the probability of an accidental needlestick. This is particularly true for "long needles" commonly used in spinal and epidural procedures in which the handle portion of the device is separated from the needle tip by a substantial distance.

Prior safety devices have been developed which include a protective guard specifically dimensioned to surround and bind a predetermined needle size. The prior safety devices have been initially stored on the needle at a location remote from the patient tip. After use, the safety device is typically advanced over the patient tip to shield the medical practitioner. In view of the fact that prior safety devices have been dimensioned to accommodate a single gauge needle, a multitude of safety devices, corresponding to all utilized needle gauges, have been necessary. This contributes to increased manufacturing costs and stocking concerns.

In addition, in medical procedures utilizing long needles, it is common practice to first insert an introducer sheath into the patient, and subsequently introduce an inner cannula therethrough. Typically, both the inner cannula and the introducer sheath include a sharp pointed profile. Since the prior safety devices have been specifically designed to accommodate a single needle gauge, medical procedures utilizing an introducer sheath and an inner cannula have typically been performed without a safety device.

SUMMARY OF THE INVENTION

The present invention is directed to a single needle guard that is capable of shielding a plurality of needle gauges. In addition, the needle guard of the present invention is capable of transitioning from a first cannula dimension, such as corresponding to the dimension of an introducer sheath, to a second cannula dimension, such as corresponding to the dimension of an inner cannula.

The present invention is directed to a needle guard including a housing defining an interior cavity, and a transitional member disposed within the interior cavity. The transitional member includes a pivoting arm having a first end and a second end, with the first end adjacent an interior portion of the housing. The transitional member also includes a needle tip sensing element, and a transverse barrier. The needle tip sensing element and the transverse barrier are oriented on opposing sides of the pivoting arm adjacent the second end.

The transitional member may include a spring arm connected to the pivoting arm at a compressible pivot point. The pivoting arm may further include a binding edge. In one configuration, the interior cavity of the housing includes a longitudinal axis, and the transitional member is transitionable from a restrained position when the needle tip sensing element is disposed on a first side of the longitudinal axis, to an activated position when the needle tip sensing element is disposed on a second side of the longitudinal axis opposing the first side. In another configuration, the pivoting arm further includes a binding edge, such that transition of the transitional member from the restrained position to the activated position articulates the binding edge at least partially across the longitudinal axis. Optionally, the needle tip sensing element may include a guide rail, and the transverse barrier may include an angled restraining tab.

In another embodiment, the present invention is directed to a device including a needle having a needle tip, and a housing disposed about a portion of the needle, defining an interior cavity structured to receive the needle therethrough. The device also includes a transitional member disposed within the interior cavity. The transitional member is adapted for transition from a restrained position when the needle tip is disposed exterior to the interior cavity to an activated position when the needle tip is housed within the interior cavity. The transitional member includes a pivoting arm disposable at least partially adjacent an interior portion of the housing, a needle tip sensing element contacting at least a portion of the needle in the restrained position, and a transverse barrier. The needle tip sensing element and the transverse barrier are oriented on opposing sides of the pivoting arm adjacent the second end.

The pivoting arm may have a first end and a second end, with the first end disposed adjacent the interior portion of the housing. The transitional member may further include a spring arm connected to the pivoting arm. The pivoting arm may also include a binding edge for contacting at least a portion of the needle in the activated position to limit the advancement of the needle tip from the housing in a distal direction. The binding edge may at least partially deform a portion of the needle in the activated position. The binding edge may restrain at least a portion of the needle against an interior portion of the housing in the activated position.

In one configuration, the interior cavity of the housing may have a longitudinal axis, and the transitional member is transitionable from a restrained position when the needle tip sensing element is disposed on a first side of the longitudinal axis to an activated position when the needle tip sensing element is disposed on a second side of the longitudinal axis opposing the first side. In another configuration, the transverse barrier of the transitional member is disposed on the first side of the longitudinal axis in the restrained position, and is disposed across the longitudinal axis in the activated position to limit advancement of the needle tip from the housing in a proximal direction. Optionally, the pivoting arm may further include a binding edge, such that transition of the transitional member from the restrained position to the activated position articulates the binding edge at least partially across the longitudinal axis.

In another embodiment, the present invention is directed to a device including a needle having a needle tip, and a housing disposed about a portion of the needle, defining an interior cavity structured to receive the needle therethrough. The device further includes a transitional member disposed within the interior cavity, adapted for transition from a restrained position to an activated position. The transitional member includes a pivoting arm having a needle tip sensing element for contacting the needle in the restrained position. The pivoting arm also has a binding edge for engaging the needle in the activated position. Transition of the transitional member from the restrained position to the activated position is initiated when contact between the needle tip sensing element and the needle is interrupted.

The pivoting arm may have a first end adjacent an interior portion of the housing and a second end. The needle tip sensing element and a transverse barrier may be oriented on opposing sides of the pivoting arm adjacent the second end. The interior cavity of the housing may have a longitudinal axis, and the transitional member may be transitionable from a restrained position when the needle tip sensing element is disposed on a first side of the longitudinal axis, to an activated position when the needle tip sensing element is disposed on a second side of the longitudinal axis opposing the first side. The transverse barrier of the transitional member may be disposed on the first side of the longitudinal axis in the restrained position, and may be disposed on the second side of the longitudinal axis in the activated position to limit advancement of the needle tip from the housing in a proximal direction. In one configuration, the binding edge limits the advancement of the needle tip from the housing in the distal direction in the activated position.

In yet a further embodiment, the present invention is directed to a method of actuating a needle guard including the step of providing a needle guard disposed about at least a portion of a needle. The needle guard includes a housing defining an interior cavity structured to receive the needle having a needle tip therethrough, and a transitional member disposed within the interior cavity. The transitional member is disposed within the interior cavity, and is adapted for transition from a restrained position to an activated position. The transitional member includes a pivoting arm having a needle tip sensing element for contacting the needle in the restrained position, and a binding edge for engaging the needle in the activated position. Transition of the transitional member from the restrained position to the activated position is initiated when contact between the needle tip sensing element and the needle is interrupted. The method further includes the step of transitioning the transitional member from the restrained position to the activated position by interrupting contact between the needle tip sensing element and the needle.

The transitional member may further include a pivoting arm having a first end adjacent an interior portion of the housing and a second end. The needle tip sensing element and a transverse barrier may be disposed adjacent the second end, and oriented on opposing sides of the pivoting arm. In one configuration, transitioning the transitional member from the restrained position to the activated position includes advancing the needle tip past the needle tip sensing element in a distal direction. In another configuration, transitioning the transitional member from the restrained position to the activated position causes the transverse barrier to transition from a first side of a longitudinal axis of the housing to a position at least partially across the longitudinal axis to limit advancement of the needle tip from the housing in a proximal direction. Optionally, the binding edge engaging the needle in the activated position limits the advancement of the needle tip from the housing in a distal direction. In a further configuration, the binding edge at least partially deforms a portion of the needle in the activated position. In yet a further configuration, the binding edge restrains at least a portion of the needle against an interior portion of the housing in the activated position.

In another embodiment, the present invention is directed to a device including a needle having a needle tip, and a housing disposed about a portion of the needle. The housing defines an interior cavity structured to receive the needle therethrough. The device also includes a transitional member disposed within the interior cavity adapted for transition from a restrained position to an activated position. The transitional member includes a pivoting housing, a needle tip sensing element for contacting the needle in the restrained position, and a transverse barrier. The device also includes a spring arm disposed within the interior cavity biasing the transitional member, and including a binding edge for engaging the needle in the activated position. The spring arm and the transitional member are separate elements, and transition of the transitional member from the restrained position to the activated position is initiated when contact between the needle tip sensing element and the needle is interrupted.

The transitional member may define a recess for accommodating at least a portion of the binding edge therein in the restrained position. The transition of the transitional member from the restrained position to the activated position may also release the binding edge from within the recess.

In yet another embodiment, a device includes a needle having a needle tip and a housing disposed about a portion of the needle. The housing defines an interior cavity structured to receive the needle therethrough. The device also includes a transitional member disposed within the interior cavity adapted for transition from a restrained position to an activated position. The transitional member includes a first binding edge for restricting movement of the needle in a proximal direction in the activated position, and a second binding edge for restricting movement of the needle in a distal direction in the activated position. The transitional member also includes a needle tip sensing element, such that transition of the transitional member from the restrained position to the activated position is initiated when contact between the needle tip sensing element and the needle is interrupted.

The transitional member may also include a contact portion having a gap therein, such that the needle tip passes through the gap during transition from the retracted position to the activated position. The first binding edge and the second binding edge may contact a portion of the needle upon passage of the needle tip through the gap.

DESCRIPTION OF THE PREFERRED EMBODIMENTS

Figure 1:
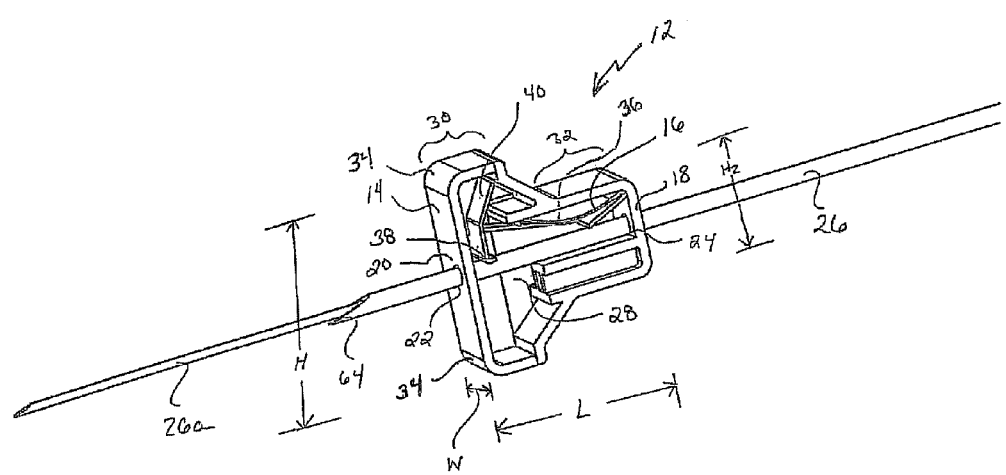
FIG. 1 is a perspective view of a needle guard in the unshielded position disposed on an introducer sheath surrounding a long needle in accordance with an embodiment of the present invention.

For purposes of the description hereinafter, the words "upper", "lower", "right", "left", "vertical", "horizontal", "top", "bottom", "lateral", "longitudinal" and like spatial terms, if used, shall relate to the described embodiments as oriented in the drawing figures. However, it is to be understood that many alternative variations and embodiments may be assumed except where expressly specified to the contrary. It is also to be understood that the specific devices and embodiments illustrated in the accompanying drawings and described herein are simply exemplary embodiments of the invention.

Figure 2:
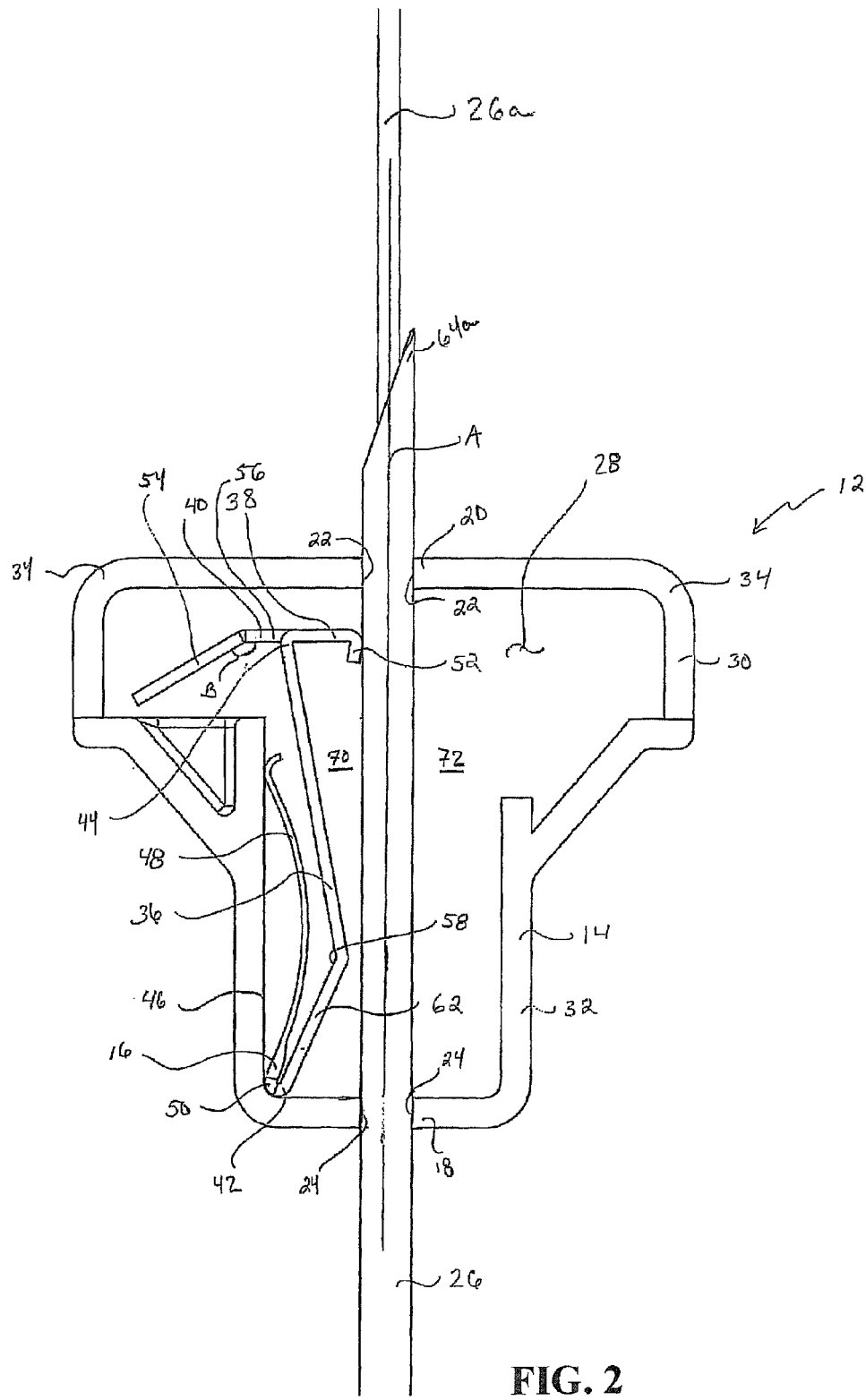
FIG. 2 is a cross-sectional side view of the needle guard of FIG. 1.

Referring to FIGS. 1-4, the needle guard 12 of the present invention includes a housing 14 and a transitional member 16 disposed within the housing 14. The housing 14 includes a first end 18 and a second end 20 opposite the first end 18, and defines an interior cavity 28 therebetween. The first end 18 defines a first port 22, and the second end 20 defines a second port 24 substantially aligned with the first port 22 along a longitudinal axis A of the housing 14, as shown in FIG. 2. The first port 22 and the second port 24 may be substantially the same size and may have substantially the same diameter.

In one embodiment, the housing 14 of the needle guard 12 is adapted to accommodate a portion of a needle cannula 26 through the first port 22 and the second port 24. In one embodiment, the first port 22 and the second port 24 may have a diameter that is slightly greater than the diameter of the needle cannula 26. In another embodiment, the first port 22 and the second port 24 may have a diameter that is considerably larger than the diameter of the needle cannula 26. The housing 14 of the needle guard 12 may accommodate a needle cannula having, for example, a diameter of from about 18 ga to about 27 ga, through the first port 22 and the second port 24. In another embodiment, the housing 14 of the needle guard 12 may accommodate multiple nested needle cannulas through the first port 22 and the second port 24, such as an outer needle cannula having an inner needle cannula nested therein. In a further embodiment, the needle guard 12 may be adapted for use with conventional gauge "long" needle(s) suitable for spinal tap procedures, and the like. Optionally, the housing 14 of the needle guard 12 is adapted to accommodate an introducer sheath having an inner cannula nested therein for delivering fluid to a patient or extracting fluid from a patient. Alternatively, the inner needle cannula may include a solid stylet for providing rigidity to an outer needle cannula.

The housing 14 may have any suitable dimensions and exterior configuration, provided the first port 22, second port 24, and at least a portion of the interior cavity 28 are sized to sufficient to accommodate the needle cannula 26 therethrough. In one embodiment, the housing 14 may have a length L, as shown in FIG. 1, of from about 0.25 inch to about 1.5 inches, a width W, shown in FIG. 1, of from about 0.09 inch to about 1 inch, and a height H, also shown in FIG. 1, of from about 0.25 inch to about 1.5 inches. In another embodiment, the housing 14 may include a first portion 30 having a height H, and a second portion 32 having a height $H_2$ that is different from the height H of the first portion 30. The housing 14 may be made of any suitable material, such as a substantially rigid polymeric composition. The housing 14 may also include a gripable region 34 having a textured surface and/or texture enhancing coated applied thereto for facilitating a medical practitioner to easily grab the housing 14.

Figure 3:
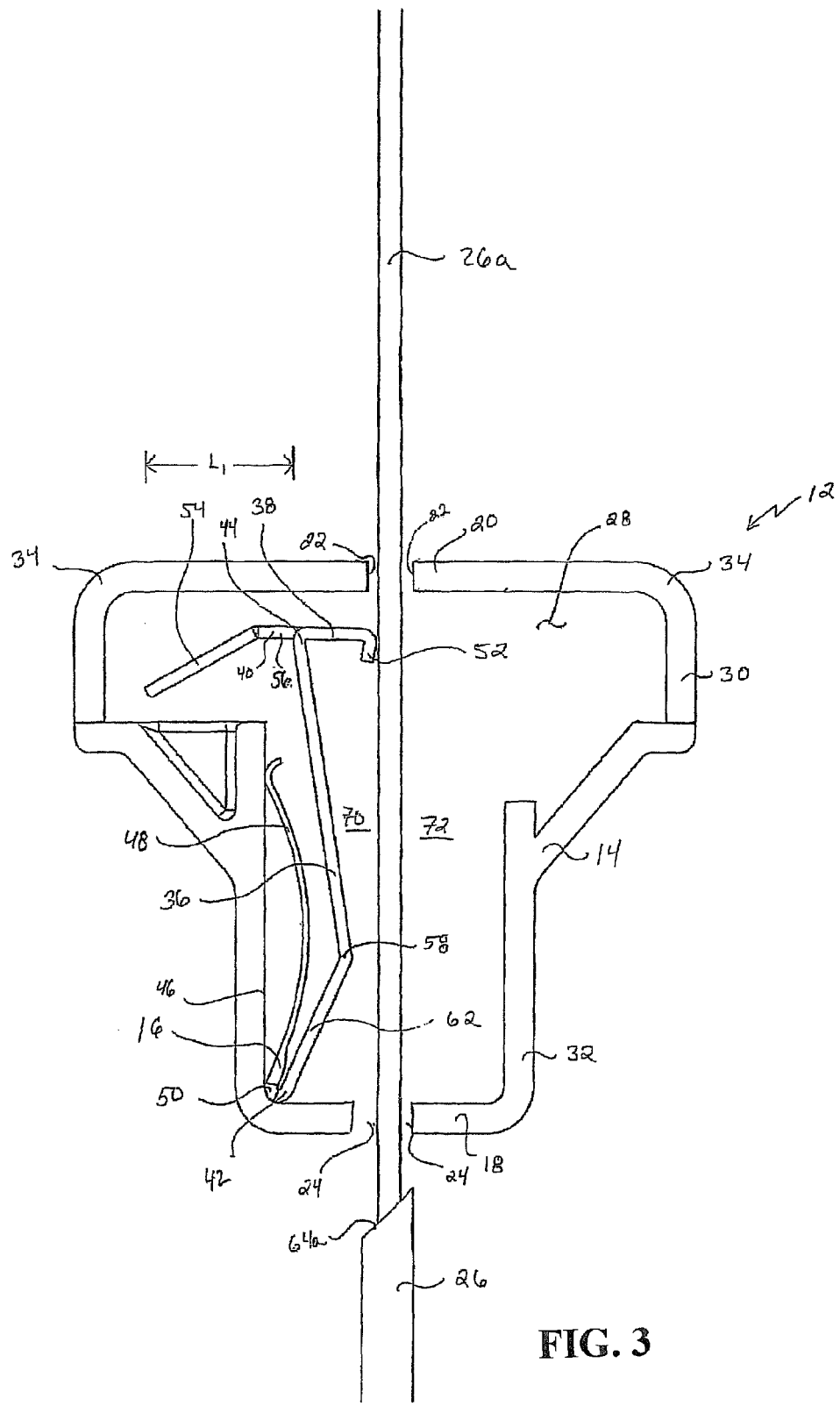
FIG. 3 is a cross-sectional side view of the needle guard of FIG. 1 advanced over the introducer sheath in accordance with an embodiment of the present invention.
Figure 4:
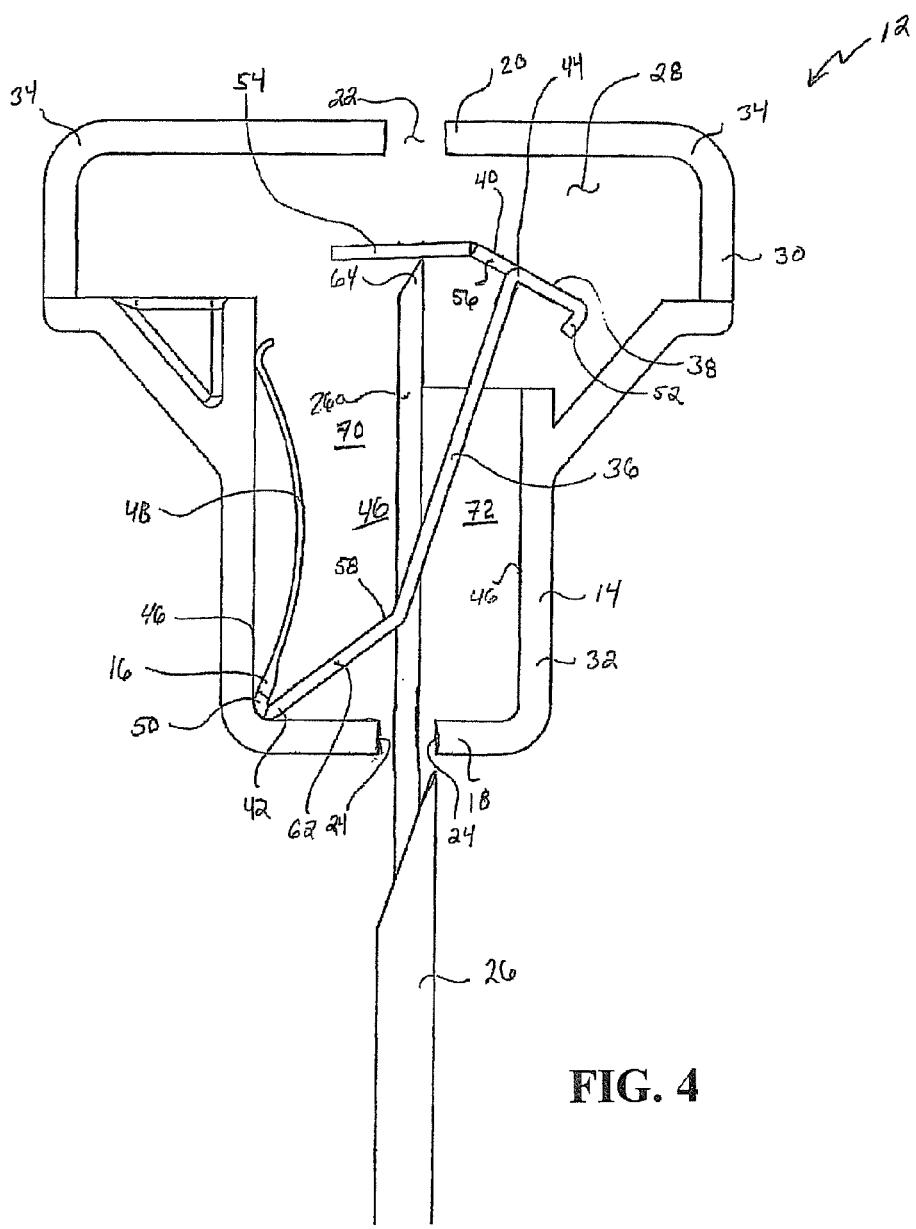
FIG. 4 is a cross-sectional side view of the needle guard of FIG. 1 in the fully-shielded position disposed on a long needle in accordance with an embodiment of the present invention.

The needle guard 12 is transitionable from an unshielded position, shown in FIGS. 1-3, to a shielded position, shown in FIG. 4, and includes a transitional member 16 disposed within the interior cavity 28 of the housing 14. The transitional member 16 includes a pivoting arm 36, a needle tip sensing element 38 oriented on one side of the pivoting arm 36, and a transverse barrier 40 oriented on the opposite side of the pivoting arm 36. The pivoting arm 36 has a first end 42 and a second end 44, with the first end 42 adjacent an interior portion, such as interior wall 46 of the housing 14. In one embodiment, the first end 42 may be secured to the interior wall 46 of the housing 14, such as adjacent the first end 18 of the housing 14. The first end 42 may be secured by conventional affixing means. In one embodiment, the pivoting arm 36 includes a spring arm 48 connected to the pivoting arm 36. The spring arm 48 may be connected to the pivoting arm 36 at a pivot point 50. The pivoting arm 36 can be biased against the interior wall 46 of the housing 14, such as against the spring arm 48 when a force is applied to a portion of the pivoting arm 36 adjacent the second end 44. The spring arm 36 may be any appropriate biasing element, such as a leaf spring, a compression spring, and/or a compressible material.

As shown in FIGS. 1-3, the second end 44 of the pivoting arm 36 can contact the needle cannula 26 and apply sufficient force adjacent the second end 44 of the pivoting arm 36 to bias the pivoting arm against the interior wall 46 of the housing 14. In one embodiment, the pivoting arm 36 and/or spring arm 48 can contain stored energy when the second end 44 of the pivoting arm 36 is in contact with the needle cannula 26. The pivoting arm 36 and the spring arm 48 may be made of the same material, or of different materials. Example materials suitable for the pivoting arm 36 include substantially rigid metals and polymeric compositions, and example materials suitable for the spring arm 48 include metals, memory metals, and resilient polymeric compositions.

Referring to FIGS. 2-5, the needle tip sensing element 38 may be disposed adjacent the second end 44 of the pivoting arm 36 of the transitional member 16, and extends in a direction toward the needle cannula 26. In one embodiment, the needle tip sensing element 38 is affixed to the pivoting arm 36 in a direction that is substantially perpendicular to the pivoting arm 36. The needle tip sensing element 38 may be made of any suitable material, and may be separately formed and subsequently attached to the second end 44 of the pivoting arm 36, or may be co-formed therewith. The needle tip sensing element 38 is adapted to contact the needle cannula 26 when the needle cannula 26 extends through both the first port 22 and the second port 24 of the housing 14. In one embodiment, the needle tip sensing element 38 includes a guide rail 52 extending from the needle tip sensing element 38 in a direction that is substantially perpendicular to the needle tip sensing element 38 and substantially parallel with the pivoting arm 36. The guide rail 52 may be adapted to contact and glide along the needle cannula 26.

The transverse barrier 40 is also disposed adjacent the second end 44 of the pivoting arm 36 and extends in a direction that is substantially opposite from the needle tip sensing element 38. In one embodiment, the transverse barrier 40 and the needle tip sensing element 38 are oriented on opposing sides of the pivoting arm 36 adjacent the second end 44. In another embodiment, the transverse barrier 40 is affixed to the pivoting arm 36 in a direction that is substantially perpendicular to the pivoting arm 36. In yet another embodiment, both the transverse barrier 40 and the needle tip sensing element 38 may be attached and/or co-formed with an end plate 60, as shown in FIGS. 5-6.

The transverse barrier 40 may be made of any suitable material, and may be separately formed and subsequently attached to the second end 44 of the pivoting arm 36, or may be co-formed therewith. In one embodiment, the transverse barrier 40 includes an angled restraining tab 54. In one embodiment, the restraining tab 54 may be connected to a base portion 56 of the transverse barrier 40 at an angle B of from about 10 degrees to about 90 degrees, as shown in FIG. 2. The angled restraining tab 54 may be fixed to the base portion 56 in such a fashion that deflection of the restraining tab 54 with respect to the base portion 56 is substantially prevented. In another embodiment, the restraining tab 54 and the base portion 56 are co-formed.

Figure 5:
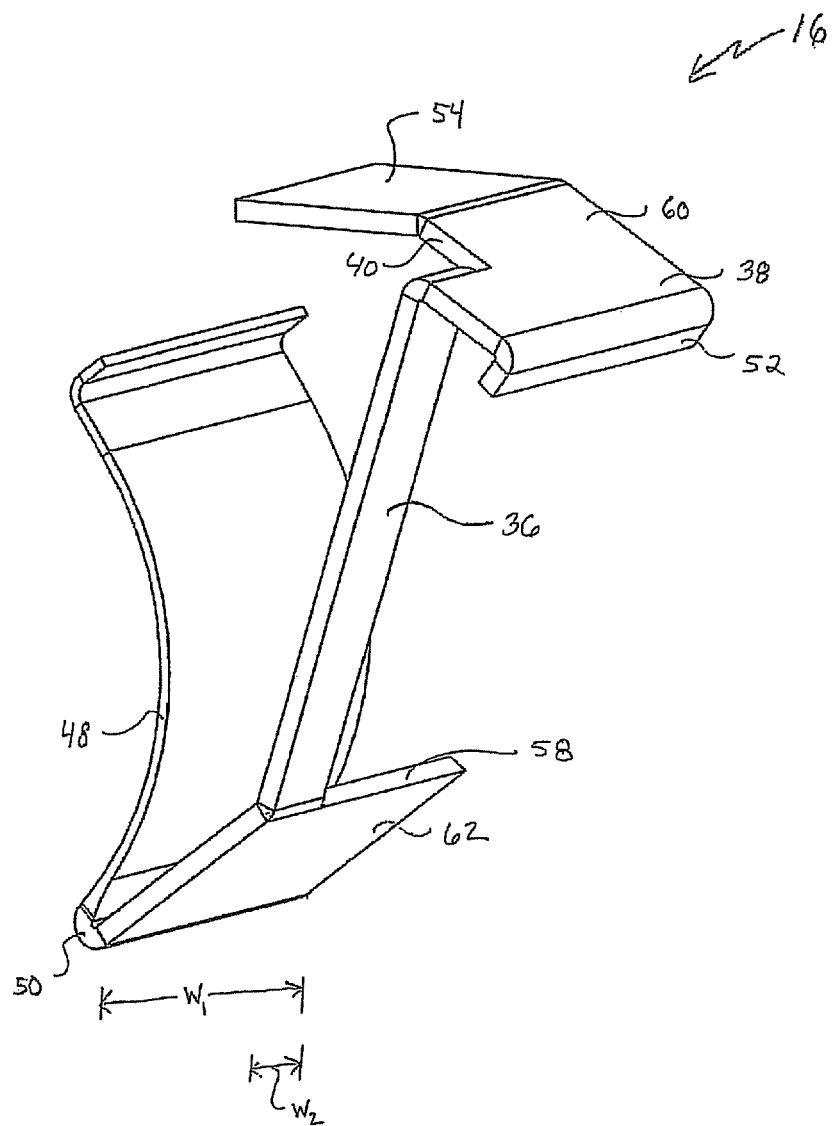
FIG. 5 is a perspective front view of the transitional member of the needle guard in accordance with an embodiment of the present invention.
Figure 6:
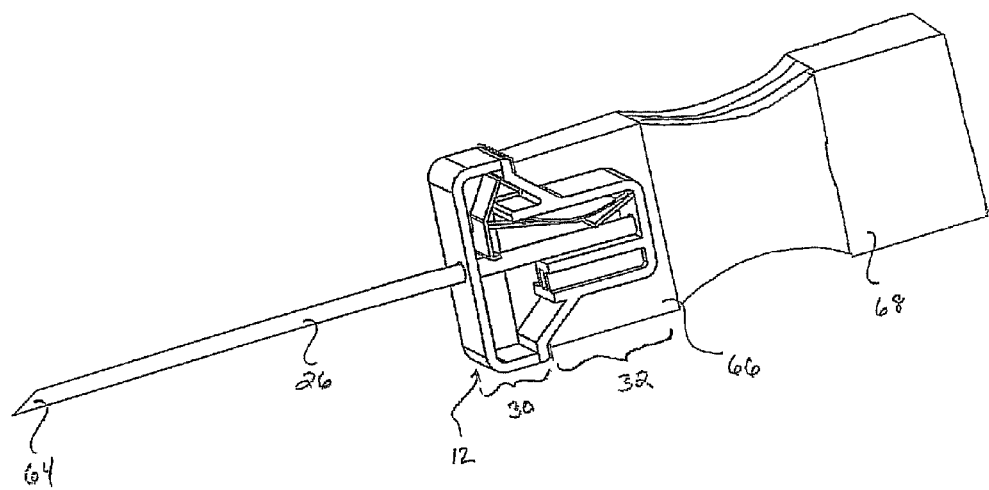
FIG. 6 is a perspective view of a needle guard nested within a hub in accordance with an embodiment of the present invention.

As shown in FIG. 5, the transitional member 16 may also include a base plate 62 connected to, or integrally formed with the pivoting arm 36, adjacent the pivot point 50 of the transitional member 16. The base plate 62 may have a width $W_1$ that is greater than the width $W_2$ of the pivoting arm 36. The base plate 62 may include a binding edge 58 positioned optionally adjacent the connection between the pivoting arm 36 and the base plate 62. The binding edge 58 may have a sharp beveled or knife-edge style ridge extending from or recessed within the base plate 62. In another embodiment, a portion of the pivoting arm 36 includes a binding edge 58 having a sharp beveled or knife-style ridge extending from or recess within a portion of the pivoting arm 36. The binding edge 58 may include any edge suitable for gripping or notching the needle cannula 26. In one embodiment, the binding edge 58 may include a blunted edge, a double beveled edge, a sharp edge disposed on opposing sides, a v-notch edge, a ridged edge such as a knurled edge and/or a curved edge.

The safety needle guard 12 of the present invention is intended to be disposed on at least a portion of a needle cannula 26, in a restrained position, during the performance of a standard medical procedure. In the restrained position, as shown in FIGS. 2-3, the needle cannula 26 is disposed through both the first port 22 and the second port 24. The needle tip sensing element 38, particularly the guide rail 52, contact the needle cannula 26 and apply force to the transitional member 16. The applied force compresses the pivoting arm 36 and the spring arm 48 against a portion of the interior wall 46 of the housing 14 through the pivot point 50. As shown in FIG. 2, the transitional member is disposed entirely on one side of the longitudinal axis A of the interior of the housing 14 in the restrained position.

Figure 7:
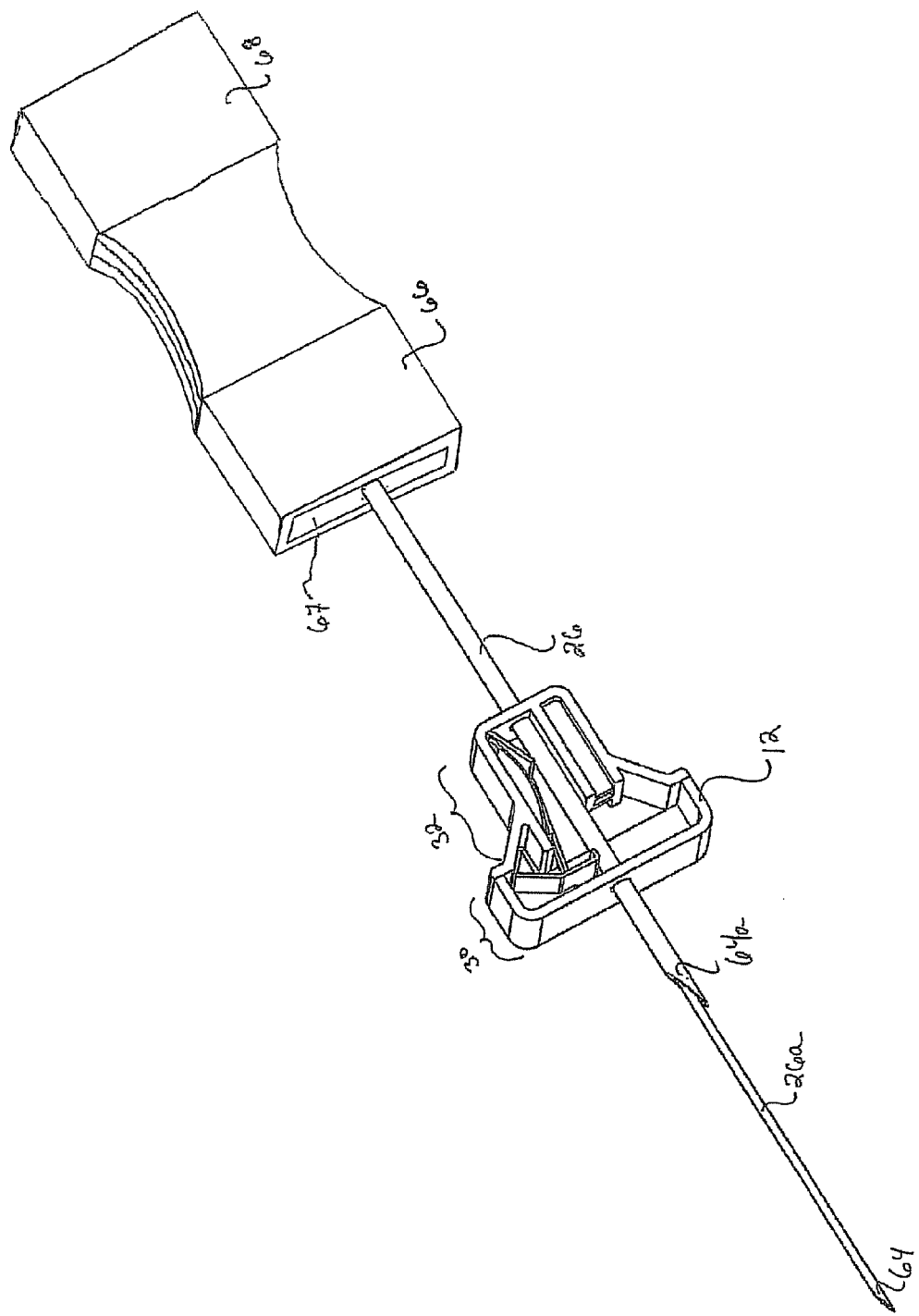
FIG. 7 is a perspective view of the needle guard of FIG. 6 removed from the hub in accordance with an embodiment of the present invention.

During a medical procedure, such as a spinal tap, epidural, and the like, a needle cannula 26, having the needle guard 12 in the restrained position disposed thereon, may be inserted into the patient. The needle guard 12 is spaced apart from the needle tip 64 or patient end of the needle cannula 26, as shown in FIGS. 1, 6, and 7. In one embodiment, as shown in FIGS. 6-7, the needle guard 12 may be nested within a portion of a needle hub 66, such as a hub interior 67, which may optionally be connected to a stylet handle 68. The hub interior 67 may be adapted to at least partially receive a portion of the needle guard 12 therein. This allows a medical practitioner to perform a medical procedure without the needle guard hindering sight lines or otherwise impeding the medical procedure. In a further embodiment, the needle guard 12 includes a first portion 30 and a second portion 32 and the hub interior 67 is adapted to receive the second portion 32 therein while restraining the first portion 30 in a location exterior to the hub interior 67. In this configuration, the medical practitioner may grasp the first portion 30 of the needle guard 12 and extract the needle guard 12 from the hub 66 and/or user handle 68 along the needle cannula 26 by manual force.

As shown in FIG. 7, the needle guard 12 can be removed from the hub interior 67 and advanced along the needle cannula 26. In one embodiment, the advancement of the needle guard 12 from the hub interior 67 can occur while the needle tip 64 is inside the patient, or after the medical procedure is completed and the needle tip 64 has been removed from the patient. During advancement of the needle guard 12 along the needle cannula 26, the transitional member 16 remains in the restrained position while the needle cannula 26 is in contact with the needle tip sensing element 38.

Once the contact between the needle tip sensing element 38 and the needle cannula 26 is interrupted, the transitional member 16 is transitioned from the restrained position, shown in FIGS. 2-3, to the activated position, shown in FIG. 4. In the restrained position, the needle tip sensing element 38 of the transitional member 16 is disposed on a first side 70 of the longitudinal axis A of the interior cavity 28 of the housing 14. When contact between the needle tip sensing element 38 and the needle cannula 26 is interrupted, the bias applied by the contact between the needle tip sensing element 38 and the needle cannula 26 is released and the transitional member 16 is transitioned to the activated position in which the needle tip sensing element 38 is disposed on a second side 72 of the longitudinal axis A of the interior cavity 28 of the housing 14, opposite the first side 70. In another embodiment, the guide rail 52 of the needle tip sensing element 38 is disposed on the first side 70 in the restrained position, and is disposed on the second side 72 after contact between the guide rail 52 and the needle cannula 26 is interrupted. In yet another embodiment, contact between the needle tip sensing element 38 and the needle cannula 26 is interrupted when the needle tip 64 passes from the exterior of the housing 14 to the interior cavity 28. In yet a further embodiment, contact between the needle tip sensing element 38 and the needle cannula 26 is interrupted when the needle tip 64 passes beyond the needle tip sensing element 38 along the longitudinal axis A in a direction from the first port 22 of the housing 14 toward the second port 24.

In the restrained position, the transverse barrier 40 of the pivoting arm 36 is disposed on the first side 70 of the longitudinal axis A of the interior cavity 28 of the housing 14 and the needle cannula 26. Once the transitional member 16 is transitioned from the restrained position to the activated position, the transverse barrier 40 of the pivoting arm 36 may be disposed toward the longitudinal axis A of the interior cavity 28 of the housing 14 in an orientation that is substantially perpendicular to the longitudinal axis A. As the needle tip 64 is drawn past the needle tip sensing element 38 in a distal direction from the first port 22 of the housing 14 toward the second port 24 of the housing 14, the pivoting arm 36 is transitioned across the longitudinal axis A. This movement aligns the transverse barrier 40 across the longitudinal axis A, thereby substantially preventing movement of the needle tip 64 in a proximal direction from the second port 24 of the housing toward the first port 22. In one embodiment, the transverse barrier 40 is dimensioned to completely obscure the first port 22 of the housing 14 in the activated position. Accordingly, once a medical practitioner advances the needle guard 12 over the needle tip 64 of the needle cannula 26, the needle tip sensing element 38 is transitioned from the restrained position to the activated position when contact between the needle cannula 26 and the needle tip sensing element 38 is interrupted. At this time, the transverse barrier 40 is disposed across the pathway of the needle cannula 26, thereby preventing unintentional advancement of the need tip 64 from the housing 14 in the proximal direction. Accordingly, the needle guard 12 of the present invention is intended to limit inadvertent advancement of the needle tip 64 from the housing 14 in the proximal direction. It is also contemplated herein that an automatic trigger (not shown) may effectuate the transition of the needle guard 12 from the restrained position to the activated position by conventional actuation means.

The needle guard 12 of the present invention is also intended to limit inadvertent removal of the needle tip 64 from the needle guard 12 in the distal direction. In one embodiment, the binding edge 58 of the pivoting arm 36 is configured such that the transition of the transitional member 16 from the restrained position to the activated position articulates the binding edge 58 towards the longitudinal axis A of the interior cavity 28 of the housing 14, as shown in FIG. 4. The binding edge 58 is configured to contact at least a portion of the needle cannula 26 in the activated position. In one embodiment, the release energy stored from the bias of the pivoting arm 36 and/or spring arm 48 against the needle cannula 26 is sufficient to cause the pivoting arm 36 to pivot toward the longitudinal axis A with enough force to cause the binding edge 58 to deform or dent at least a portion of the needle cannula 26. In one embodiment, the binding edge 58 limits the advancement of the needle tip 64 from the interior cavity 28 of the housing 14 in the distal direction by pinning a portion of the needle cannula 26 against a portion of the interior wall 46 of the housing 14. In another embodiment, the binding edge 58 at least partially restrains a portion of the needle cannula 26 against a portion of the housing 14 due to a frictional interference therewith. In yet another embodiment, the binding edge 58 itself may at least partially deform or dent against a portion of the needle cannula 26, thereby restraining the needle cannula 26 against a portion of the housing 14. In yet a further embodiment, the application of additional force to the needle cannula 26 increases the interference between the binding edge 58 and the needle cannula 26, thereby further restricting movement of the needle cannula 26 within the housing 14. It is also contemplated herein, that multiple binding edges 58, as similarly described herein, may be employed to further restrict movement of the needle cannula 26 within the housing 14. It is further contemplated herein that the geometry of the needle guard 12 is configured such that the binding mechanism may be self-locking or wedging. For example, once binding is initiated any force applied to the needle cannula 26 in a substantially proximal direction increases the binding force.

Referring once again to FIGS. 1-7, an advantage of the present invention is the ability to use a single needle guard over needle cannulas having many different diameters. Since the transitional member 16 is located on only one side of the longitudinal axis A in the restrained position, the needle guard 12 can accept any size needle cannula 26, which is limited only by the diameter of the first port 22 of the housing 14.

Another advantage of the present invention is the ability of the needle guard 12 to accommodate nested needle cannulas 26, 26a. Referring again to FIG. 7, in certain procedures it is desirable to advance a first needle cannula 26 into a patient, such as an introducer sheath, and to subsequently advance a second needle cannula 26a into the patient through the first needle cannula 26. In this situation, it is desirable to shield the needle tip 64 of the second needle cannula 26a, as this needle tip is withdrawn from the patient in an exposed condition, whereas the needle tip 64a of the first needle cannula 26 is "blunted" by the presence of the second needle cannula 26a therethrough.

The needle guard 12 of the present invention can effectively "jump" from a larger diameter needle cannula 26 to a smaller diameter needle cannula 26a, as shown in FIG. 3, without transitioning from the restrained position to the activated position. As shown in FIG. 2, the needle sensing tip element 38 contacts the first needle cannula 26. The second needle cannula 26a is nested within the first needle cannula 26. When the needle guard 12 is advanced over the needle tip 64a of the first needle cannula 26, the needle tip sensing element 38 biases against the second needle cannula 26a, thereby preventing transition to the activated position. Since the activation mechanism of the present needle guard 12 rides on one side of the needle cannula(s) 26, 26a in the restrained position, transition from the restrained position to the activated position is not triggered until the last nested needle cannula 26, 26a passes along the longitudinal axis A past the needle tip sensing element 38. In another embodiment, it is contemplated herein that multiple nested needle cannulas, such as three, four, or five needle cannulas, may be used with the needle guard of the present invention.

Figure 8:
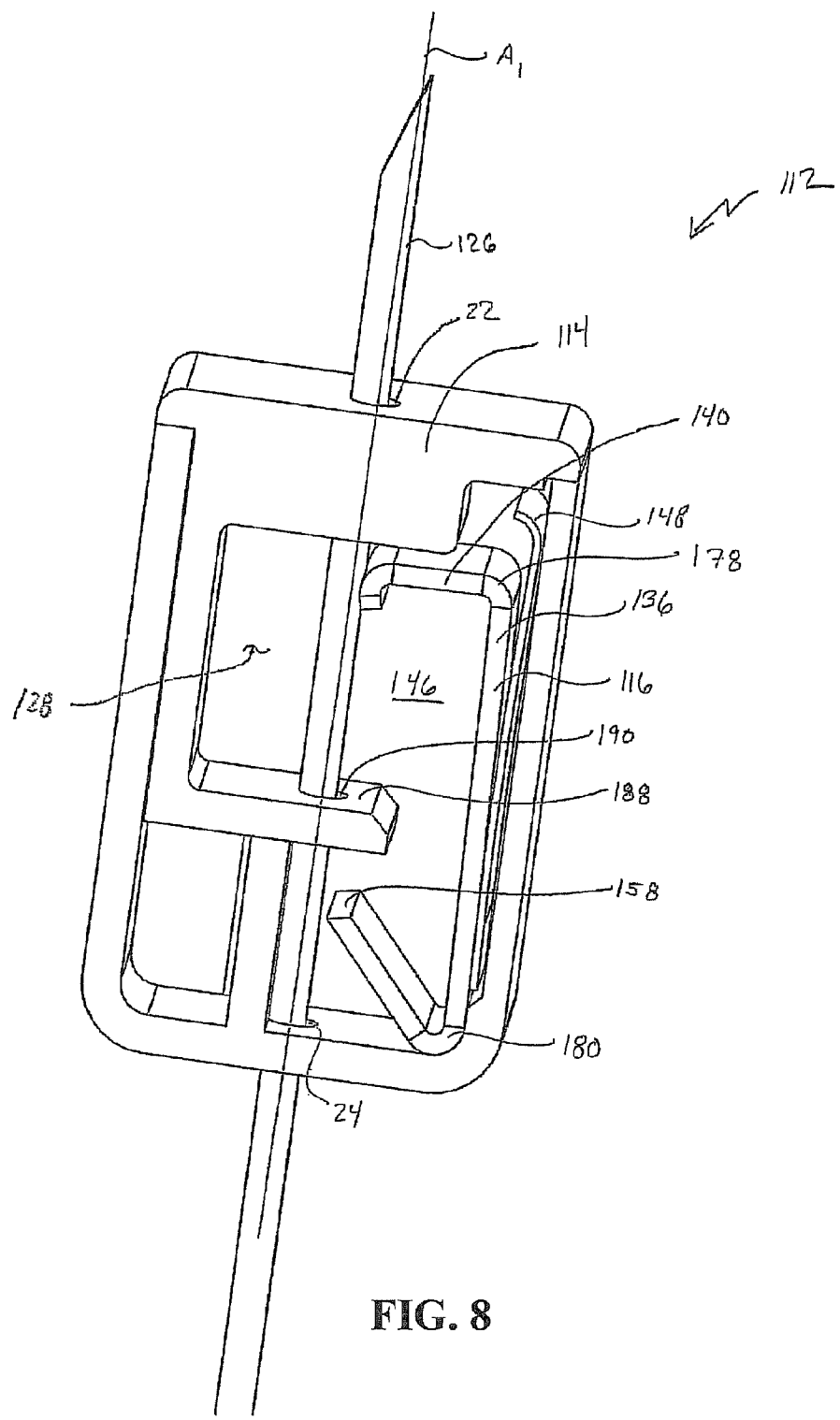
FIG. 8 is a perspective cross-sectional side view of an alternative embodiment of a needle guard in the unshielded position disposed on a long needle in accordance with an embodiment of the present invention.
Figure 9:
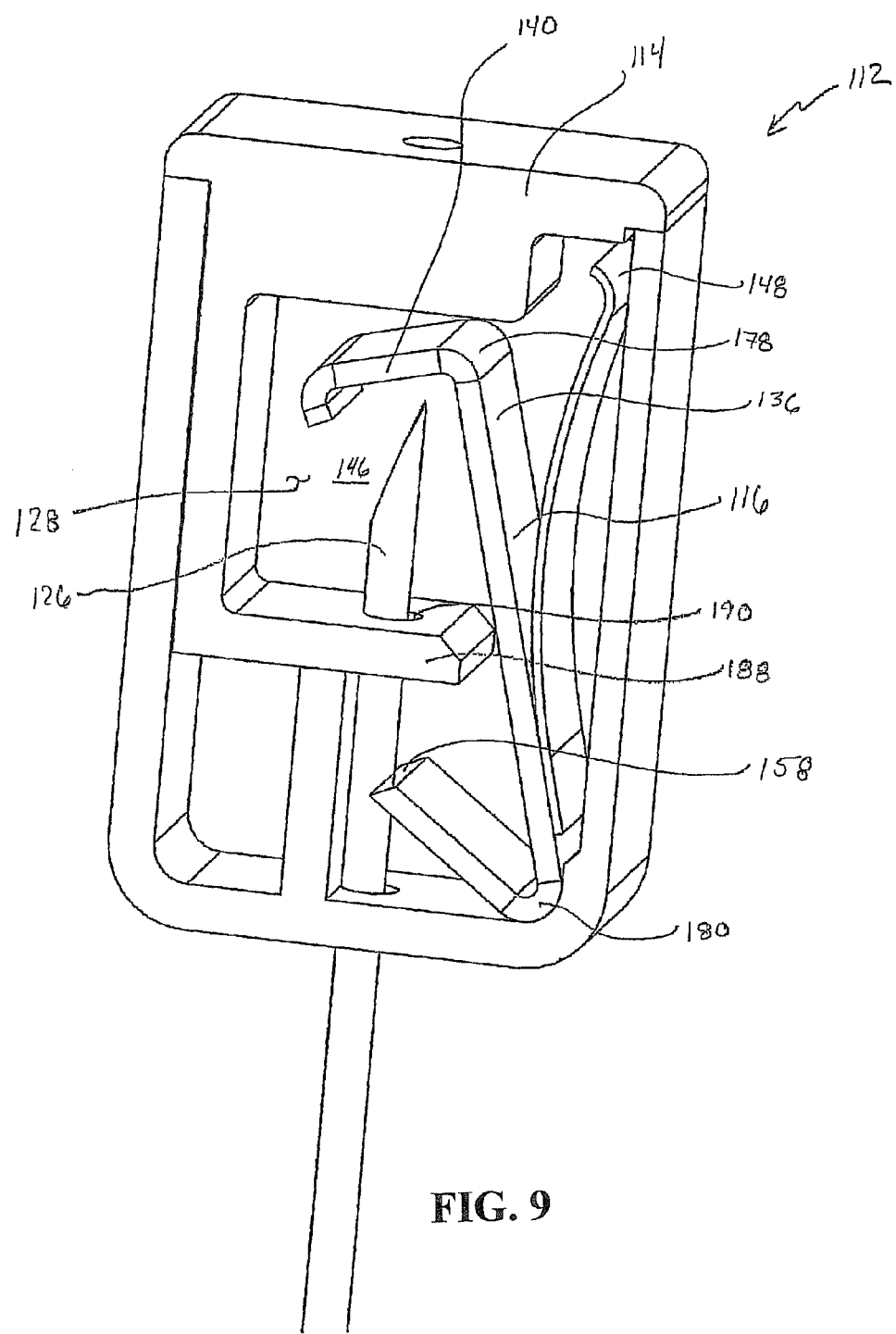
FIG. 9 is a perspective cross-sectional side view of the needle guard of FIG. 8 in the fully-shielded position disposed on a long needle.

In an alternative embodiment of the present invention, shown in FIGS. 8-9, the needle guard 112 includes a housing 114 having an interior cavity 128 and a transitional member 116 disposed within the interior cavity 128. The transitional member 116 is similarly shown in FIGS. 1-7, and includes a pivoting arm 136, a spring arm 148, and a transverse barrier 140 as described above. Referring again to FIGS. 8-9, the binding edge 158 is disposed adjacent the opposite end of the pivoting arm 136 from the transverse barrier 140. As shown in FIGS. 8-9, the transverse barrier 140 and the binding edge 158 are disposed on the same side of the pivoting arm 136 at opposite ends, such as the transverse barrier 140 disposed adjacent the first end 178 and the binding edge disposed adjacent the second end 180. Both the transverse barrier 140 and the binding edge 158 are disposed on a first side of the longitudinal axis $A_1$ of the interior cavity 128 of the housing 114 in the restrained position. Optionally, the housing 114 may include a retaining bar 188 having a port 190 disposed therein for providing stability to the needle cannula 126. As described above with reference to FIGS. 1-7, the first port 22 and the second port 24 may be similarly sized. The port 190 may likewise be sized to correspond to the dimensions of the first port 22 and the second port 24.

As shown in FIG. 8, in the restrained position, the binding edge 158 does not contact the needle cannula 126. As shown in FIG. 9, transition of the transitional member 116 from the restrained position to the activated position causes the binding edge to swing toward and contact the needle cannula 126. As described above, this contact may deform the needle cannula 126 and pin the needle cannula 126 against a portion of an interior wall 146 of the housing 114, thereby preventing inadvertent advancement of the needle tip 164 from the interior cavity 128 of the housing 114.

In yet another embodiment of the present invention, shown in FIGS. 10-13, a needle guard 312 includes a housing 314 having an interior cavity 328 with a transitional member 316 disposed within the interior cavity 328. The transitional member 316 includes a first binding edge 358, a second binding edge 360, a spring arm 348 and a needle tip sensing element 350. In this embodiment, two binding edges 358, 360 are employed to prevent movement of a needle cannula 326 in either the proximal direction or the distal direction after transition from the restrained position to the activated position. The present embodiment employs a second binding edge 360 in place of a transverse barrier, as discussed above. In another embodiment, a transverse barrier, as discussed above, may also be included in the device of FIGS. 10-13 in addition to the second binding edge 360 as a secondary locking measure.

As also described above, the needle guard 312 is dimensioned to receive a single needle cannula 327 or nested needle cannulas 326, 326a therein. In one embodiment, the needle guard 312 is dimensioned to accommodate a first needle cannula 326, such as an introducer sheath, therein and to subsequently accommodate a second needle cannula 326a, having a smaller diameter therein.

Figure 10:
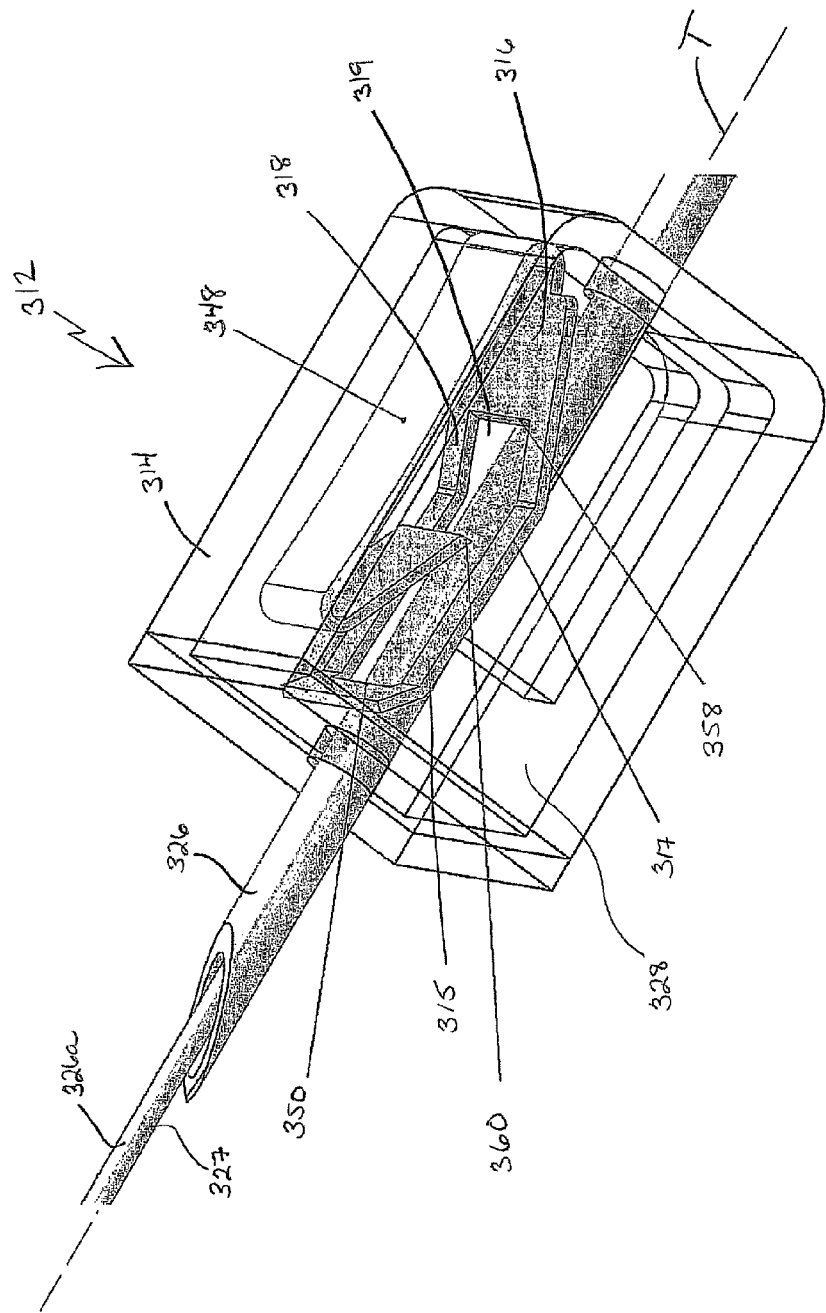
FIG. 10 is a perspective view of a needle guard in an unshielded position in accordance with an alternative embodiment of the present invention.
Figure 11:
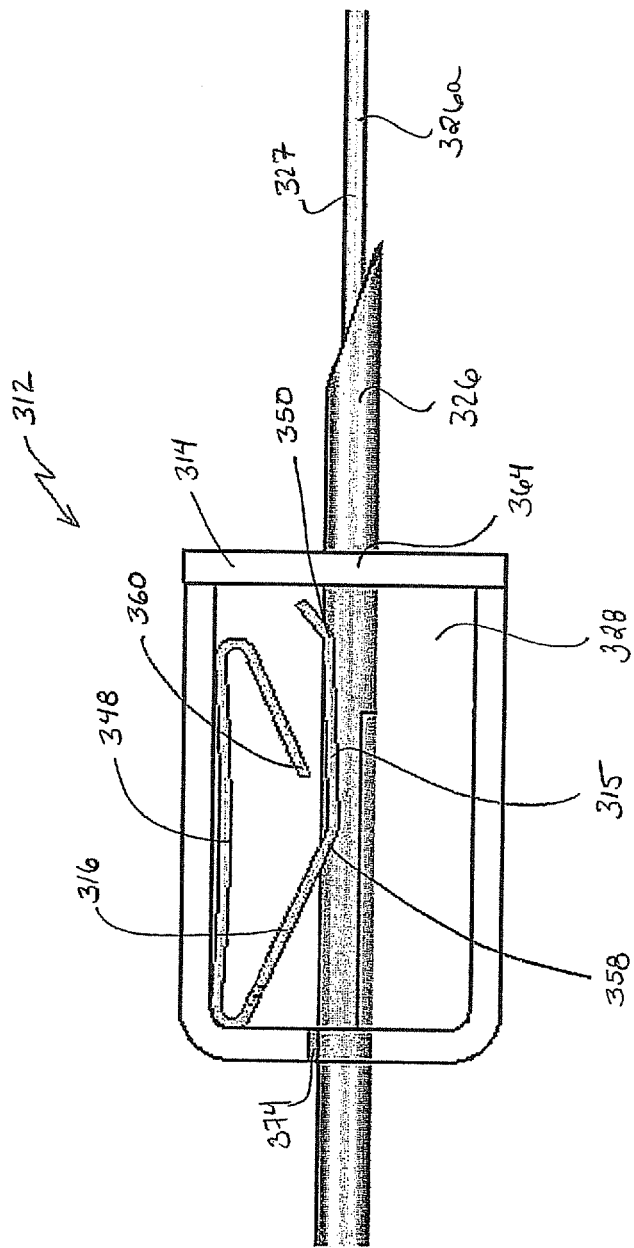
FIG. 11 is a side view of the needle guard of FIG. 10.

As shown in FIGS. 10-11, in the retracted position the transitional member 316 may be oriented on a single side of the longitudinal axis T with at least a portion of the needle tip sensing element 350 contacting the needle cannula 327, 326. As shown in FIGS. 10-11, in the restrained position, needle cannula 327, such as the nested cannula 326, 326a, may be disposed through the first port 364 of the housing 314 with the spring arm 348 biasing the transitional member 316 against a portion of the needle cannula 327, 326. A contact portion 315 of the transitional member 316 may include a first arm portion 317 and a second arm portion 318 separated by a gap 319. The first binding edge 358 may be disposed between the first arm portion 317 and the second arm portion 318, such as along the proximal edge of the gap 319, as shown in FIG. 10. The needle tip sensing element 350 may also be disposed between the first arm portion 317 and the second arm portion 318, such as along the distal edge of the gap 319, also shown in FIG. 10. In the retracted position, at least a portion of the contact portion 315, such as at least one of the first arm portion 317 and the second arm portion 318 are provided adjacent the needle cannula 327, 326a. Optionally, at least a portion of the contact portion 315, such as at least one of a portion of the first arm portion 317 and the second arm portion 318, may ride along the needle cannula 327, 326a in the restrained position.

Figure 12:
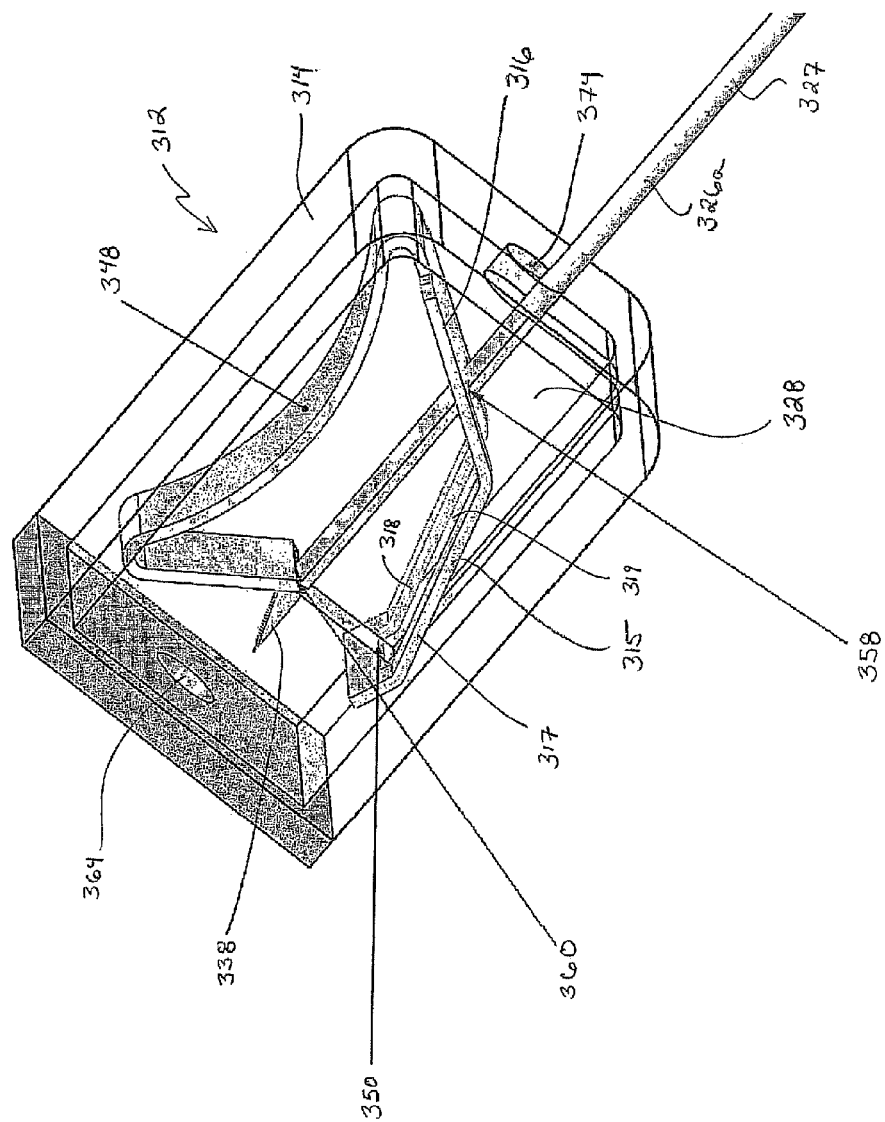
FIG. 12 is a perspective view of the needle guard of FIG. 10 in the shielded position.
Figure 13:
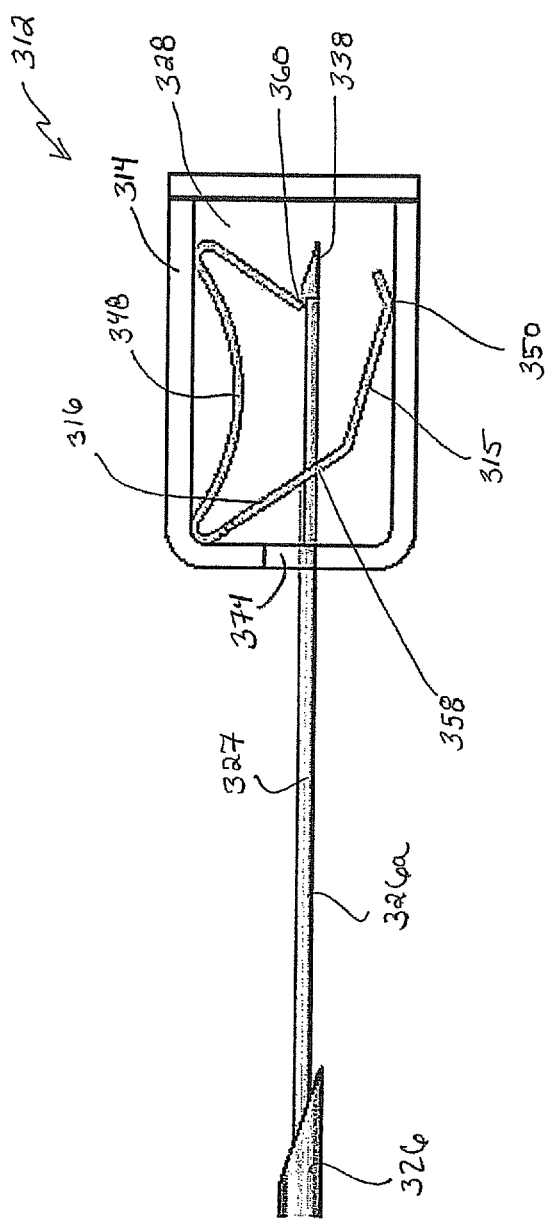
FIG. 13 is a side view of the needle guard of FIG. 12.

As shown in FIGS. 12-13, once the distal tip 338 of the needle cannula 327, or the distal tip 338 of a second needle cannula 326a nested within a first needle cannula 326, as described herein, is withdrawn from the first port 364 of the housing 348, the spring arm 314 biases the transitional member 316 toward the needle cannula 326. As shown in FIG. 13, the contact portion 315 of the transitional member 316 may pass around or over a portion of the needle cannula 327, 326a. In one embodiment, the needle cannula 327, 326a may pass through the gap 319 defined between the first arm portion 317 and the second arm portion 318 during transition of the transitional member from the restrained position to the activated position. As the needle cannula 327, 326a, such as the distal tip 338, passes through the gap 319, the first binding edge 358 contacts the needle cannula 327, 326a and prevents the needle cannula 327, 326a from moving in a proximal direction from the interior of the housing 314. As also described herein, the first binding edge 358 may deform or dent the needle cannula 327, 326a such that the needle cannula 327, 326a cannot be removed from within the housing 314 through the second port 374. In another embodiment, the first binding edge 358 restrains the needle cannula 327 or 326a against a portion of the interior of the housing 314 in a frictional resistance. In yet another embodiment, the first binding edge 358 may deform about at least a portion of the needle cannula 327 or 326a thereby preventing removal of the needle cannula 327 or 326a from the housing 314 in the proximal direction. In a further configuration, the contact portion 315 may include a single arm 317 and the gap 319 may be defined by a sole arm 317. It is noted herein that the needle tip sensing element 350, as shown in FIGS. 10-13 is similarly described above with reference to sensing element 38 shown in FIGS. 1-7.

As also shown in FIGS. 12-13, as the distal tip 338 of the needle cannula 327 or 326a passes through the gap 319 the second binding edge 360 contacts the needle cannula 327, 326a and prevents the needle cannula 327, 326a from moving in a distal direction from the interior of the housing 314. In one embodiment, as shown in FIGS. 10-11, the second binding edge 360 contacts the contact portion 315, such as at least one of the first arm portion 317 and the second arm portion 318 in the restricted position. Alternatively, the second binding edge 360 may be biased away from the needle cannula 327, 326a by the spring arm 348 in the restricted position. During transition of the transitional member 316 from the restricted position, shown in FIGS. 10-11, to the activated position, shown in FIGS. 12-13, the contact portion 315 pivots away from the needle cannula 327, 326a and the second binding edge 360 contacts a portion of the needle cannula 327, 326a. The second binding edge 360 may deform or dent the needle cannula 327, 326a such that the needle cannula 327, 326a cannot be removed from within the housing 314 through the first port 364. In another embodiment, the second binding edge 360 restrains the needle cannula 327 or 326a against a portion of the interior of the housing 314 in a frictional resistance. In yet another embodiment, the second binding edge 360 may deform about at least a portion of the needle cannula 327 or 326a thereby preventing removal of the needle cannula 327 or 326a from the housing 314 in the distal direction. In yet a further embodiment, the first binding edge 358 contacts the needle cannula 327, 326a at a location proximal to the location at which the second binding edge 360 contacts the needle cannula 327, 326a.

Figure 14:
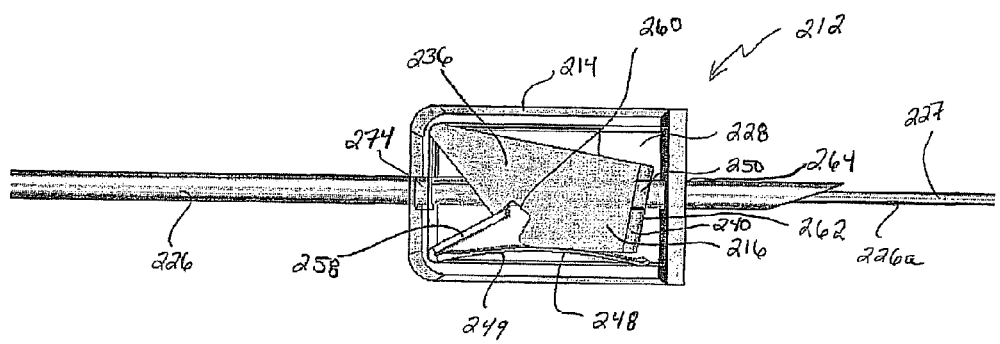
FIG. 14 is a side view of a needle guard in an unshielded position in accordance with an alternative embodiment of the present invention.
Figure 15:
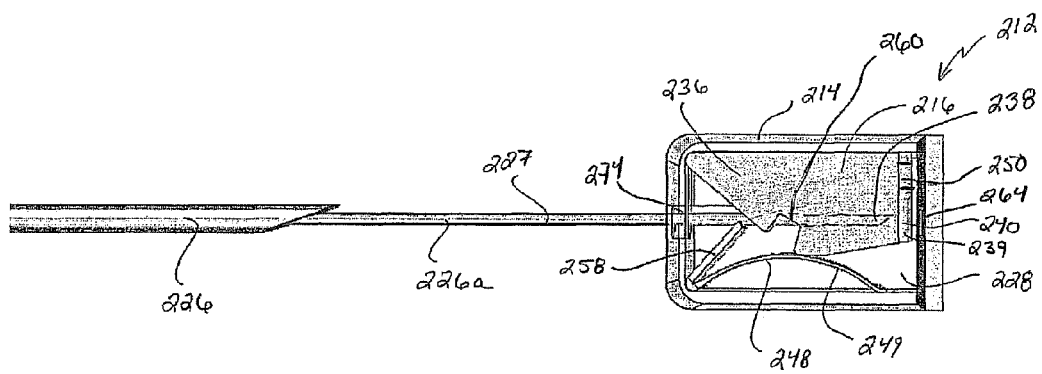
FIG. 15 is a side view of the needle guard of FIG. 14 in the shielded position.

In yet another embodiment of the present invention, shown in FIGS. 14-15, a needle guard 212 includes a housing 214 having an interior cavity 228 with a transitional member 216 and a spring arm 248 disposed within the interior cavity 228. The transitional member 216 includes a pivoting housing 236, a needle tip sensing element 250 and a transverse barrier 240. The spring arm 248 includes a biasing portion 249 and a binding edge 258. In this embodiment, the needle tip sensing element 250 and transverse barrier 240 are located in a separate component from the binding edge 258. Specifically, the needle tip sensing element 250 is integral with the transitional member 216 and the binding edge 258 is integral with the spring arm 248.

As also described above, the needle guard 212 is dimensioned to receive a single needle cannula 227 or nested needle cannulas 226, 226a therein. In one embodiment, the needle guard 212 is dimensioned to accommodate a first needle cannula 226, such as an introducer sheath, therein and to subsequently accommodate a second needle cannula 226a, having a smaller diameter therein.

As shown in FIG. 14, the transitional member 216 may include a recess 260 dimensioned to accommodate at least a portion of the binding edge 258 therein in the restrained position. The transitional member 216 also includes a needle tip sensing element 250 disposed within a distal face 262, such that the needle tip sensing element 250 is aligned with a first port 264 of the housing 214 in the restrained position. As shown in FIG. 14, in the restrained position, the nested cannula 226, 226a may be disposed through the first port 264 of the housing 214 and the needle tip sensing element 250. The transitional member 216 is biased against the nested cannula 226, 226a extending therethrough, by the spring arm which is disposed on one side of the needle when the transition member is in the retrained position.

As shown in FIG. 15, once the distal tip 238 of the needle cannula 227, or the distal tip 238 of a second needle cannula 226a nested within a first needle cannula 226, as described herein, is withdrawn from the first port 264 of the housing 214 and the needle tip sensing element 250 loses contact with the needle cannula 227, the spring arm 248 biases the transitional member 216 toward a portion of the housing 214 such that the distal tip 238 is no longer aligned through the needle tip sensing element 250. As shown in FIG. 15, the distal tip 238 then aligns with a restraining portion 239 of the distal face 262 of the transitioning member 216, thereby preventing re-advancement of the distal tip 238 through the first port 264 of the housing 214. As the transitioning member 216 is biased toward a portion of the housing 214, the binding edge 258 becomes unseated from within the recess 260 of the transitioning member 216 and binds against a portion of the needle cannula 227 or nested needle cannula 226a. As also described herein, the binding edge 258 may deform or dent the needle cannula 227 or 226a such that the needle cannula 226 cannot be removed from within the housing 214 through the second port 274. In another embodiment, the binding edge 258 restrains the needle cannula 227 or 226a against a portion of the interior of the housing 214 in a frictional resistance. In yet another embodiment, the binding edge 258 may deform about at least a portion of the needle cannula 227 or 226a thereby preventing removal of the needle cannula 227 or 226a from the housing 214.

By separating the needle tip sensing element 250 and the binding edge 258, the sensitivity of the needle guard 212 may be increased. Optionally, this configuration may reduce the overall dimensions required to fabricate the needle guard and/or may increase the needle guard 212 capacity to receive and bind a larger range of cannula gauges therein.

While the present invention is described with reference to several distinct embodiments of a needle guard and method of use, those skilled in the art may make modifications and alterations without departing from the scope and spirit. Accordingly, the above detailed description is intended to be illustrative rather than restrictive.

What is claimed is:

1. A needle guard, comprising:
   a housing defining an interior cavity; and
   a transitional member disposed within the interior cavity, the transitional member comprising:
   a pivoting arm having a first end and a second end, the first end adjacent an interior portion of the housing,
   a needle tip sensing element connected to the pivoting arm, and
   a transverse barrier, wherein the needle tip sensing element extends radially outward from and substantially perpendicular to a first side of the pivoting arm adjacent the second end and the transverse barrier extends radially outward from and substantially perpendicular to a second side of the pivoting arm adjacent the second end in a direction opposite from a direction in which the needle tip sensing element extends, the first side opposite the second side.

2. The needle guard of claim 1, wherein the transitional member further comprises a spring arm connected to the pivoting arm at a compressible pivot point.

3. The needle guard of claim 1, wherein the pivoting arm further comprises a binding edge.

4. The needle guard of claim 1, wherein the interior cavity of the housing includes a longitudinal axis, and the transitional member is transitionable from a restrained position when the needle tip sensing element is disposed on a first side of the longitudinal axis, to an activated position when the needle tip sensing element is disposed on a second side of the longitudinal axis opposing the first side.

5. The needle guard of claim 4, wherein the pivoting arm further comprises a binding edge, such that transition of the transitional member from the restrained position to the activated position articulates the binding edge at least partially across the longitudinal axis.

6. The needle guard of claim 1, wherein the needle tip sensing element further comprises a guide rail.

7. The needle guard of claim 1, wherein the transverse barrier further comprises an angled restraining tab.

8. A device, comprising:
   a needle having a needle tip;
   a housing disposed about a portion of the needle, defining an interior cavity structured to receive the needle therethrough along a longitudinal axis of the interior cavity of the housing; and
   a transitional member disposed within the interior cavity, adapted for transition from a restrained position when the needle tip is disposed exterior to the interior cavity to an activated position when the needle tip is housed within the, interior cavity, the transitional member comprising:
   a pivoting arm having a first end and a second end, the pivoting arm disposable at least partially adjacent an interior portion of the housing,
   a needle tip sensing element biased against at least a portion of the needle in the restrained position, and
   a transverse barrier, wherein the needle tip sensing element extends radially outward from and substantially perpendicular to a first side of the pivoting arm adjacent the second end and the transverse barrier extends radially outward from and substantially perpendicular to a second side of the pivoting arm adjacent the second end in a direction opposite from a direction in which the needle tip sensing element extends, the first side opposite the second side, wherein the transitional member is disposed entirely on one side of the longitudinal axis of the interior cavity of the housing in the restrained position.

9. The device of claim 8, wherein the pivoting arm has a first end and a second end, the first end adjacent the interior portion of the housing.

10. The device of claim 8, wherein the transitional member further comprises a spring arm connected to the pivoting arm.

11. The device of claim 8, wherein the pivoting arm further comprises a binding edge for contacting at least a portion of the needle in the activated position to limit the advancement of the needle tip from the housing in a distal direction.

12. The device of claim 11, wherein the binding edge at least partially deforms a portion of the needle in the activated position.

13. The device of claim 11, wherein the binding edge restrains at least a portion of the needle against an interior portion of the housing in the activated position.

14. The device of claim 8, wherein the interior cavity of the housing has a longitudinal axis and the transitional member is transitionable from a restrained position when the needle tip sensing element is disposed on a first side of the longitudinal axis to an activated position when the needle tip sensing element is disposed on a second side of the longitudinal axis opposing the first side.

15. The device of claim 14, wherein the transverse barrier of the transitional member is disposed on the first side of the longitudinal axis in the restrained position, and is disposed across the longitudinal axis in the activated position to limit advancement of the needle tip from the housing in a proximal direction.

16. The device of claim 14, wherein the pivoting arm further comprises a binding edge, such that transition of the transitional member from the restrained position to the activated position articulates the binding edge at least partially across the longitudinal axis.

17. A device, comprising:
a needle having a needle tip;
a housing disposed about a portion of the needle, defining an interior cavity structured to receive the needle therethrough along a longitudinal axis of the interior cavity of the housing; and
a transitional member adapted for transition from a restrained position to an activated position and disposed entirely on one side of the longitudinal axis of the interior cavity of the housing in the restrained position, the transitional member comprising:
a pivoting arm having a needle tip sensing element continuously biased against the needle in the restrained position, and a binding edge for engaging the needle in the activated position, wherein transition of the transitional member from the restrained position to the activated position is initiated when contact between the needle tip sensing element and the needle is interrupted, and wherein the transitional member moves across the longitudinal axis of the interior cavity of the housing in a substantially downward direction relative to the housing during transition of the transitional member from the restrained position to the activated position.

18. The device of claim 17, wherein the pivoting arm has a first end adjacent an interior portion of the housing and a second end, and the needle tip sensing element and a transverse barrier oriented on opposing sides of the pivoting arm adjacent the second end.

19. The device of claim 18, wherein the interior cavity of the housing has a longitudinal axis and the transitional member is transitionable from a restrained position when the needle tip sensing element is disposed on a first side of the longitudinal axis to an activated position when the needle tip sensing element is disposed on a second side of the longitudinal axis opposing the first side.

20. The device of claim 19, wherein the transverse barrier of the transitional member is disposed on the first side of the longitudinal axis in the restrained position, and is disposed on the second side of the longitudinal axis in the activated position to limit advancement of the needle tip from the housing in a proximal direction.

21. The device of claim 17, wherein the binding edge limits the advancement of the needle tip from the housing in the distal direction in the activated position.

22. A method of actuating a needle guard, comprising the steps of:
providing a needle guard disposed about at least a portion of a needle, the needle guard comprising:
a housing defining an interior cavity structured to receive the needle having a needle tip therethrough along a longitudinal axis of the interior cavity of the housing, and
a transitional member adapted for transition from a restrained position to an activated position and disposed entirely on one side of the longitudinal axis of the interior cavity of the housing in the restrained position, the transitional member comprising:
a pivoting arm having a needle tip sensing element continuously biased against the needle in the restrained position, and a binding edge for engaging the needle in the activated position, wherein transition of the transitional member from the restrained position to the activated position is initiated when contact between the needle tip sensing element and the needle is interrupted; and
transitioning the transitional member from the restrained position to the activated position by interrupting contact between the needle tip sensing element and the needle, wherein the transitional member moves across the longitudinal axis of the interior cavity of the housing in a substantially downward direction relative to the housing when the transitional member is transitioned from the restrained position to the activated position.

23. The method of claim 22, wherein the transitional member further comprises a pivoting arm having a first end adjacent an interior portion of the housing and a second end, the needle tip sensing element and a transverse barrier adjacent the second end and oriented on opposing sides of the pivoting arm.

24. The method of claim 23, wherein transitioning the transitional member from the restrained position to the activated position includes advancing the needle tip past the needle tip sensing element in a distal direction.

25. The method of claim 24, wherein transitioning the transitional member from the restrained position to the activated position causes the transverse barrier to transition from a first side of a longitudinal axis of the housing to a position at least partially across the longitudinal axis to limit advancement of the needle tip from the housing in a proximal direction.

26. The method of claim 22, wherein the binding edge engaging the needle in the activated position limits the advancement of the needle tip from the housing in a distal direction.

27. The method of claim 22, wherein the binding edge at least partially deforms a portion of the needle in the activated position.

28. The method of claim 22, wherein the binding edge restrains at least a portion of the needle against an interior portion of the housing in the activated position.

29. A device, comprising:
a needle having a needle tip;
a housing disposed about a portion of the needle, defining an interior cavity; and
a transitional member adapted for transition from a restrained position to an activated position, the transitional member comprising a pivoting housing, a needle tip sensing element for contacting the needle in the restrained position, and a transverse barrier; and
a spring arm disposed within the interior cavity biasing the transitional member, the spring arm comprising a binding edge for engaging the needle in the activated position, the spring arm disposed entirely on one side of the needle within the interior cavity when the transitional member is in the restrained position, wherein the spring arm and the transitional member are separate elements, and wherein transition of the transitional member from the restrained position to the activated position is initiated when contact between the needle tip sensing element and the needle is interrupted, and wherein, in the restrained position, the needle extends through the needle tip sensing element.

30. The device of claim 29, wherein the transitional member defines a recess for accommodating at least a portion of the binding edge therein in the restrained position.

31. The device of claim 30, wherein transition of the transitional member from the restrained position to the activated position releases the binding edge from within the recess.

32. A device, comprising:
a needle having a needle tip;
a housing disposed about a portion of the needle, defining an interior cavity structured to receive the needle therethrough along a longitudinal axis of the interior cavity of the housing; and
a transitional member adapted for transition from a restrained position to an activated position and disposed entirely on one side of the longitudinal axis of the interior cavity of the housing in the restrained position, the transitional member comprising:
  a first binding edge for restricting movement of the needle in a proximal direction in the activated position,
  a second binding edge for restricting movement of the needle in a distal direction in the activated position, and
  a needle tip sensing element, wherein transition of the transitional member from the restrained position to the activated position is initiated when contact between the needle tip sensing element and the needle is interrupted.

33. The device of claim 32, wherein the transitional member further comprises a contact portion having a gap therein, wherein the needle tip passes through the gap during transition from the retracted position to the activated position.

34. The device of claim 33, wherein the first binding edge and the second binding edge contact a portion of the needle upon passage of the needle tip through the gap.

* * * * *